(12) United States Patent
Pile-Spellman et al.

(10) Patent No.: US 9,463,113 B2
(45) Date of Patent: Oct. 11, 2016

(54) SYSTEMS AND METHODS FOR INTRAVASCULAR COOLING

(71) Applicant: Hybernia Medical LLC, Pelham, NY (US)

(72) Inventors: John Pile-Spellman, Pelham, NY (US); Erwin Lin, Whitestone, NY (US)

(73) Assignee: HYBERNIA MEDICAL LLC, Pelham, NY (US)

( * ) Notice: Subject to any disclaimer, the term of this patent is extended or adjusted under 35 U.S.C. 154(b) by 576 days.

(21) Appl. No.: 13/714,744

(22) Filed: Dec. 14, 2012

(65) Prior Publication Data

US 2013/0331916 A1 Dec. 12, 2013

Related U.S. Application Data

(60) Division of application No. 12/143,361, filed on Jun. 20, 2008, now Pat. No. 8,343,097, which is a continuation of application No. PCT/US2006/045374, filed on Nov. 22, 2006.

(60) Provisional application No. 60/753,433, filed on Dec. 22, 2005.

(51) Int. Cl.
| | |
|---|---|
| *A61F 7/12* | (2006.01) |
| *A61M 1/36* | (2006.01) |
| *A61M 5/172* | (2006.01) |
| *A61M 5/44* | (2006.01) |
| *A61F 7/00* | (2006.01) |

(52) U.S. Cl.
CPC .............. *A61F 7/12* (2013.01); *A61M 1/369* (2013.01); *A61M 5/1723* (2013.01); *A61M 5/44* (2013.01); *A61F 2007/0059* (2013.01); *A61F 2007/0096* (2013.01); *A61F 2007/126* (2013.01); *A61M 2205/3368* (2013.01); *A61M 2205/3606* (2013.01)

(58) Field of Classification Search
CPC .............. A61F 2007/0059; A61F 2007/0096; A61F 2007/126; A61F 7/12; A61M 1/369; A61M 2205/3368; A61M 2205/3606; A61M 5/1723; A61M 5/44
USPC ........................................................ 604/113
See application file for complete search history.

(56) References Cited

U.S. PATENT DOCUMENTS

| | | | | |
|---|---|---|---|---|
| 5,984,893 A | * | 11/1999 | Ward ................ | A61M 5/16827 128/DIG. 12 |
| 2004/0167467 A1 | * | 8/2004 | Harrison ................... | A61F 7/12 604/113 |
| 2005/0107741 A1 | * | 5/2005 | Willard ..................... | A61F 7/12 604/113 |

* cited by examiner

*Primary Examiner* — Jason Flick

(74) *Attorney, Agent, or Firm* — Antonio Papageorgiou, Esq.; Meister Seelig & Fein LLP

(57) ABSTRACT

Methods and systems for infusing a cooled infusate to a target location in a patient are described. A temperature of the blood and infusate admixture upstream of the catheter as well as at other locations along the catheter may be monitored and a feedback system utilized to control the volume, temperature, and/or infusion rate of the infusate so as to achieve a predetermined temperature at the target location. Control may also be based on the patient's native vessel flow rate. The system may monitor or calculate hematocrit upstream of the catheter and adjust infusion so as to provide sufficient oxygenation of the blood and infusate admixture. The system may also monitor reflux of the infusate past a distal end of the catheter and reduce infusion upon the detection of reflux.

14 Claims, 10 Drawing Sheets

SYSTEMS AND METHODS FOR INTRAVASCULAR COOLING

CROSS-REFERENCE TO RELATED APPLICATIONS

This application is a continuation-in-part of and claims the benefit of and priority to International Patent Application Serial No. PCT/US2006/045374, filed on Nov. 22, 2006, which claims the benefit of and priority to U.S. Provisional Patent Application Ser. No. 60/753,433, filed on Dec. 22, 2005, both of which are expressly incorporated herein in their entireties by reference thereto.

FIELD OF THE INVENTION

The present invention is directed to systems and methods for intravascular cooling. More particularly, the present invention relates to intravascular cooling catheter systems and methods useful for cooling an organ such as the brain or other tissue.

BACKGROUND INFORMATION

Organs of the human body, such as the brain, kidney, and heart, are maintained at a constant temperature of approximately 37° C. Cooling is believed to be the most effective ischemia mitigator. More particularly, cooling of organs below 35° C. is believed to provide cellular protection from anoxic damage caused by a disruption of blood supply or by trauma. Also, cooling can reduce internal or external swelling associated with traumatic injuries.

Hypothermia is currently a useful medical tool and is sometimes performed to protect the brain or other organs from injury. Cooling of the brain is generally accomplished through whole body cooling to create a condition of total body hypothermia in the range of from 20° to 30° C. This cooling is accomplished by immersing a patient in ice, by using cooling blankets, or by cooling the blood flowing externally through a cardiopulmonary bypass machine. U.S. Pat. No. 3,425,419 ("Dato") and U.S. Pat. No. 5,486,208 ("Ginsburg") describe catheters for cooling the blood by circulating a cold fluid to create total body hypothermia. The systems of Dato and Ginsburg, however, are believed to be unsuitable for selective organ hypothermia because they do not provide for selective organ cooling. Hypothermia is achieved by circulating a cold fluid within each of the Dato and Ginsburg catheters, which are designed to be used in the great vessels like the inferior vena cava. Even if the catheters are placed in a selective vessel supplying an organ, there would be no manner of detecting when a desired temperature has been reached because there is no feedback system regarding the effect of the catheter on the selected organ temperature.

Use of total body hypothermia to provide organ protection is believed to have a number of drawbacks. First, it may create cardiovascular problems, such as cardiac arrhythmias, reduced cardiac output, and increased systemic vascular resistance, which side effects can result in organ damage. These side effects are believed to be caused reflexively in response to the reduction in core body temperature. Second, total body hypothermia is difficult to administer. Immersing a patient in ice water has its associated problems. Placement on cardiopulmonary bypass requires surgical intervention and specialists to operate the machine, and this procedure is associated with a number of complications, including bleeding and volume overload. And third, the time required to reduce the body temperature and the organ temperature is prolonged. Minimizing the time between injury and the onset of cooling is believed to produce better clinical outcomes.

Some physicians are believed to have immersed a patient's head in ice to provide brain cooling. Also, there are cooling helmets, or head gear, to perform a similar function. This approach suffers from the problems of slow cool down and poor temperature control due to the temperature gradient that must be established externally to internally. It is believed that complications associated with total body cooling, such as arrhythmia and decreased cardiac output, can be caused by cooling of the face and head only.

Selective organ hypothermia has been studied. See, for example, A. E. Schwartz et al., "Isolated Cerebral Hypothermia by Single Carotid Artery perfusion of Extracorporeally Cooled Blood in Baboons", Neurosurgery, Vol. 39, No. 3, September 1996, pp. 577-582, and A. E. Schwartz et al., "Selective Cerebral Hypothermia by Means of Transfemoral Internal Carotid Artery Catheterization," Radiology, Vol. 201, No. 2, November 1996, pp. 571-572. Utilizing baboons, blood is circulated and cooled externally from the body via the femoral artery and returned to the body through the carotid artery. These studies are believed to show that the brain could be selectively cooled to temperatures of 20° C. without reducing the temperature of the entire body. Subsequently, cardiovascular complications associated with total body hypothermia are not believed to have occurred.

Selective organ hypothermia is believed to have been attempted by perfusing an organ with a cold solution, such as saline or a perfluorocarbon. A type of selective organ hypothermia referred to as cardioplegia is performed to protect the heart during heart surgery. Cardioplegia has a number of drawbacks, including limited time of administration due to excessive volume accumulation, cost and inconvenience of maintaining the perfusate, lack of effectiveness due to temperature dilution from the blood, lack of a method to monitor hemodilation, and the decrease in the hematocrit of the blood supply to selected organs. Temperature dilution by the blood is a particular problem in high blood flow organs such as the brain. For cardioplegia, the blood flow to the heart is minimized; therefore, temperature dilution is minimized.

A conventional cooling catheter is believed to employ a feedback system to control the temperature of the cooled infusate. There is believed to be a need, however, for an intravascular system and method for corporeal cooling which provides for a more accurate and effective control of the volume and temperature of the cooled infusate and which is safer for the patient.

SUMMARY

According to an exemplary embodiment of the present invention, a device may include an insertion device, such as a catheter, adapted to fluidicly communicate with a source of an infusate and a controller. The controller may be adapted to control at least one of (a) a temperature of the infusate, (b) an infusion rate of the infusate through the insertion device, and (c) a volume of the infusate passing through the insertion device, in accordance with a temperature of a blood and infusate mixture downstream relative to an infusate exit location of the insertion device while the insertion device is placed in a blood vessel of a patient for infusion of the infusate, and in accordance with at least one of (a) a temperature of the infusate at or adjacent the exit location, (b) a temperature upstream and adjacent the exit location, and (c) a core body temperature of the patient. The infusate flows through the insertion device and, assuming no reflux or a substantial absence of reflux, through the blood vessel in a downstream direction.

Upstream refers to a direction opposite the direction of flow of infusate through the insertion device, when the insertion device is passed into a blood vessel in the direction of blood flow, and refers to the same direction in which the infusate flows through the insertion device, when the insertion device is passed into a blood vessel in a direction opposite the blood flow. For example, in the context of catheter used to cool the brain and inserted through a groin vascular access site in the common femoral artery and navigated to one of the common carotid arteries, as detailed below, the term upstream herein refers to the direction towards the aortic arch and the term downstream herein refers to the direction towards the internal carotid artery. Further, in the context of a catheter used to cool a patient's leg and inserted through a groin vascular access site in the common femoral artery and navigated into the common iliac artery, as detailed below, the term upstream herein refers to the direction towards the aorta and the term downstream herein refers to the direction towards the common femoral artery.

The device may include a plurality of temperature sensors, wherein the controller is adapted to receive signals from the temperature sensors. At least one of the temperature sensors may be positioned downstream relative to the infusate exit location and may be adapted to measure a temperature of the infusate and blood mixture. At least another one of the temperature sensors may be adapted to measure at least one of (a) a temperature of the infusate at or adjacent the exit location, (b) a temperature upstream and adjacent the exit location, and (c) a core body temperature of the patient.

The temperature sensors may be at least one of (a) connected to the insertion device, (b) connected to a second device, and (c) connected to both the insertion device and the second device. The second device may be at least one of (a) arranged adjacent to the insertion device, (b) connected to the insertion device, and (b) arranged so as to extend through the insertion device.

The controller may be adapted to control at least one of (a) the temperature of the infusate, (b) the infusion rate of the infusate through the insertion device, and (c) the volume of the infusate passing through the insertion device to at least one of detect and control a temperature of the infusate and blood mixture. The flow of infusate may be maintained, e.g., for a predetermined period of time and/or until reflux is detected.

The insertion device may be in fluid communication with the source of infusate.

The device may further include a pump or valve controlled by the controller and adapted to provide or direct infusate from the infusate source through the insertion device.

The device may further include a first valve, adapted to control flow of infusate from a first infusate reservoir through the insertion device, and a second valve, adapted to control flow of infusate from a second infusate reservoir through the insertion device. The temperatures of the first and second infusate reservoirs may be different and the device may be configured to control the temperature of the infusate flowing through the insertion device via coordinated control of both the first valve and the second valve.

The device may further include a heat exchanger controlled by the controller and adapted to control the temperature of the infusate.

The device may further include a guide catheter adapted to be disposed about the catheter.

The device may further include an insulator disposed about the insertion device.

The guide catheter may be configured to enlarge from a first low profile to a second larger profile so as to at least one of create and increase in size an insulating annular space between the catheter and the guide catheter.

The temperature sensor adapted to measure temperature upstream and adjacent the exit location may be located, for example, about 0.2 cm to about 5 cm upstream the exit location.

The controller may be adapted to control at least one of (a) an infusion rate of the infusate through the insertion device and (b) a volume of infusate passing through the insertion device in accordance with an admixture, i.e., mixture of blood an infusate, hematocrit, e.g., downstream of the exit location.

The controller may be adapted to calculate at least one of a dilution of the blood and an admixture hematocrit, e.g., downstream the exit location, using a base whole body hematocrit of the patient and a dilution of the patient's blood.

The controller may be adapted to calculate at least one of a dilution of the blood and an admixture hematocrit, downstream the exit location using, the equation (Hct)*(1−dF), wherein Hct is a base whole body hematocrit of the patient, dF is the dilution of the blood and is represent by the following equation dF=(infusion rate)/(infusion rate+X), and X is an amount of blood per unit time at the core body temperature in the blood and infusate mixture, and may be represented by the equation X=(infusion rate*$(T_1-T_2)/(T_4-T_1)$), e.g., when there is no reflux, wherein $T_1$ is a temperature of the blood and infusate mixture downstream the exit location, $T_2$ is a temperature of the infusate at or adjacent the exit location, $T_3$ is temperature adjacent to and upstream the exit location, and $T_4$ is the core body temperature of the patient.

The controller may also be configured to (i) accept as input from a clinician the whole body Hct of the patient at the beginning of the cooling procedure, and (ii) to account for Hct dilution throughout the cooling procedure so as to assure accurate admixture Hct calculation. The controller may account for Hct dilution by taking into account the volume of infusate added to the patient's blood and the volume of the infusion fluid output by the patient, e.g., through urination.

The controller may be configured to adjust the Hct according to a computerized function such as that disclosed in M. A. Neimark, A. A. Konstas, A. F. Laine, J. Pile-Spellman, "Integration of jugular venous return and circle of willis in a theoretical human model of selective brain cooling," J. Appl. Physiol., 103: 1848-1856, 2007 (first published Aug. 30, 2007), equation 6 on page 4, which references A. A. Konstas, M. A. Neimark, A. F. Laine, J. Pile-Spellman, "A theoretical model of selective cooling using intracarotid cold saline infusion in the human brain," J. Appl. Physiol., 102: 1329-1340, 2007 (first published Dec. 14, 2006), equation 6 page 3. Both of these articles are herein incorporated in their entireties by reference thereto.

The temperature sensors may include a first temperature sensor positioned downstream relative to an infusate exit location of the catheter and adapted to measure a temperature of an infusate and blood mixture when the catheter is placed in a blood vessel of a patient for infusion of the infusate, a second temperature sensor adapted to measure a temperature of the infusate at or adjacent the exit location, a third temperature sensor adapted to measure a temperature outside the catheter upstream and adjacent the exit location, and a fourth temperature sensor adapted to measure a core body temperature of the patient.

The device may further include a heat exchanger or an infusate pump. The controller may be adapted to receive signals from the temperature sensors and to control the heat exchanger and/or the pump in accordance with the signals from the plurality of temperature sensors.

The controller may be adapted to calculate at least one parameter, e.g., a temperature, of the infusate at or adjacent the exit location.

The controller may be adapted to calculate the temperature of the infusate at least one of at and adjacent the exit location using at least one of (a) the temperature of the infusate outside the patient, (b) the infusion rate of the infusate through the insertion device, and (c) a property, e.g., a surface area and/or a thermal conductivity, of the insertion device.

The device may include a source of first infusate and a source of second infusate. The catheter may be in fluid communication with the source of the first infusate and in fluid communication with the source of the second infusate. The controller may be adapted to control the temperature of the infusate by control of a relative proportion of the first infusate and second infusate passing through the catheter.

The device may include at least one pump controlled by the controller and adapted to provide the first infusate from the source of first infusate and the second infusate from the source of second infusate through the catheter.

The device may include a first heat exchanger controlled by the controller and adapted to control the temperature of the first infusate and a second heat exchanger controlled by the controller and adapted to control the temperature of the second infusate.

The controller may be adapted to control the at least one of (a) the temperature of the infusate, (b) the infusion rate of the infusate through the insertion device, and (c) the volume of the infusate passing through the insertion device to cause the blood and infusate mixture to at least one of reach and fall below a predetermined target temperature.

According to an exemplary embodiment of the present invention, a device may include an insertion device adapted to fluidicly communicate with a source of an infusate, a plurality of sensors, and a controller. The controller may be adapted to receive signals from the sensors indicative of at least one parameter of a bodily fluid and to control at least one of (a) at least one parameter of the infusate, (b) an infusion rate of the infusate through the insertion device, and (c) a volume of the infusate passing through the insertion device, in accordance with the signals from the sensors. At least one of the sensors may be positioned downstream relative to an infusate exit location of the insertion device. At least another one of the sensors may be adapted to measure at least one of (a) the at least one parameter of the infusate at or adjacent the exit location, (b) the at least one parameter upstream and adjacent the exit location, and (c) a core body temperature of the patient.

The controller may be adapted to control at least one parameter of the infusate corresponding to the at least one parameter of the bodily fluid.

The controller may be adapted to control at least one parameter of the infusate which is different than the at least one parameter of the bodily fluid.

The controller may be adapted to control at least one of the (a) the at least one parameter of the infusate, (b) an infusion rate of the infusate through the insertion device, and (c) the volume of the infusate passing through the insertion device to at least one of detect and control the at least one parameter of the bodily fluid for a predetermined period of time.

The controller may be adapted to control at least one of (a) an infusion rate of the infusate through the insertion device and (b) a volume of infusate passing through the insertion device in accordance with an admixture hematocrit, e.g., downstream of the exit location.

According to an exemplary embodiment of the present invention, a device may include an insertion device adapted to be inserted into a system and fluidicly communicate with a source of an infusate, a sensor located exterior to an internal lumen of the insertion device and proximally away from an infusate exit location of the insertion device, and a controller. The controller may be adapted to receive signals from the sensor indicative of at least one parameter of a system fluid, e.g., a bodily fluid such as blood, and to control at least one of (a) at least one parameter of the infusate, (b) an infusion rate of the infusate through the insertion device, and (c) a volume of the infusate passing through the insertion device in accordance with the signals from the sensor.

The sensor may be a temperature sensor and the controller may be adapted to receive signals from the temperature sensor and to control at least one of (a) a temperature of the infusate, (b) an infusion rate of the infusate through the insertion device, and (c) a volume of the infusate passing through the insertion device in accordance with the signals from the temperature sensor. The sensor may be located, for example, about 0.2 cm to about 5 cm proximal the exit location.

The system may be a patient's vasculature filled with blood and the controller may be adapted to calculate a native vessel flow rate (nvFR) in a blood vessel in which the insertion device may be inserted.

The system may be adapted to monitor the nvFR, e.g., monitor a plateau in the value of the native vessel flow rate.

The controller may be adapted to at least one of stop, maintain, reduce, and increase infusion of the infusate into the patient based on the nvFR. For example, the controller may increase the flow or decrease the temperature of the cooled infusate if the rate of change of nvFR remains below a predetermined value.

The controller may also be adapted to at least one of stop, maintain, and reduce infusion of the infusate into the patient upon detection of the plateau in the value of the native vessel flow rate.

According to an exemplary embodiment of the present invention, a device may include an insertion device adapted to fluidicly communicate with a source of an infusate, and a controller. The controller may be adapted to control at least one of (a) an infusion rate of the infusate through the insertion device into a patient and (b) a volume of infusate passing through the insertion device in accordance with an admixture hematocrit, e.g., downstream of an infusate exit location of the insertion device in the patient.

The device may include a calculation device adapted to calculate an admixture hematocrit, e.g., downstream of the infusate exit location, based on a measurement of a base whole body hematocrit.

The device may include a calculation device adapted to calculate an admixture hematocrit, e.g., upstream of the infusate exit location, based on a measurement of a base whole body hematocrit.

The controller may be configured to calculate the admixture hematocrit at least one of (a) upstream and (b) downstream of the infusate exit location.

The device may include a temperature sensor positioned downstream relative to the infusate exit location and adapted to measure a temperature of an infusate and blood mixture when the insertion device is placed in a blood vessel of a patient for infusion of the infusate. The controller may be adapted to receive a signal from the temperature sensor and to calculate the admixture hematocrit, e.g., downstream of the infusate exit location, in accordance with the signals from the temperature sensor.

The controller may be adapted to control at least one of (a) a temperature of the infusate, (b) an infusion rate of the infusate through the insertion device, and (c) a volume of the infusate passing through the insertion device, in accordance with the signal from the temperature sensor.

In another embodiment of the invention, a wire for use in an intravascular system, may include a longitudinally extending wire member and at least one temperature sensor. The wire member may have a distal end, a proximal end, and an outer surface and having at least one temperature sensor arranged on said outer surface. The at least one temperature sensor on the wire may be capable of communicating signals to a controller that controls an infusion pump. The first temperature sensor on the wire may be positioned on the distal end of the wire and may be capable of measuring the temperature of a mixture of cooled infusate and blood. A second temperature sensor on the wire may be positioned proximal to the first temperature sensor and may be capable of measuring the temperature of cooled infusate. A third temperature sensor on the wire may be positioned proximal to the second temperature sensor and may be capable of measuring the temperature of any reflux. An optional fourth temperature sensor on the wire may be positioned proximal to the third temperature sensor and may be capable of determining a patient's core temperature.

According to an exemplary embodiment of the present invention, a device may include: i) an elongate sensor support device adapted to be inserted into a patient and having one or more sensors connected to it along its length; and ii) a controller adapted to receive signals from the sensors and control at least one of (a) at least one parameter of an infusate infused into the patient through an insertion device in a downstream direction, (b) an infusion rate of the infusate, and (c) a volume of the infusate, in accordance with at least one parameter of a blood and infusate mixture downstream relative to an infusate exit location of the insertion device while the insertion device is placed in a blood vessel of a patient with a downstream flow of blood for infusion of the infusate, and in accordance with at least one of (a) at least one parameter of the infusate at least one of at and adjacent the exit location, (b) at least one parameter of the infusate upstream and adjacent the exit location, and (c) a core body temperature of the patient.

The controller may be adapted to control a temperature of the infusate in accordance with (1) a temperature of a blood and infusate mixture downstream relative to the infusate exit location of the insertion device, and (2) at least one of (a) the temperature of the infusate at least one of at and adjacent the exit location, (b) the temperature of the infusate upstream and adjacent the exit location, and (c) a core body temperature of the patient.

According to an exemplary embodiment of the present invention, a device may include: i) an elongate sensor support device adapted to be inserted into a patient and having one or more sensors connected to it along its length; and ii) a controller adapted to receive signals from the sensors and control at least one of (a) at least one parameter of an infusate infused into the patient through an insertion device in a downstream direction, (b) an infusion rate of the infusate, and (c) a volume of the infusate, in accordance with at least one parameter of a blood and infusate mixture upstream and adjacent an infusate exit location on the insertion device.

The sensors may be temperature sensors and the controller may be adapted to receive temperature signals from the sensors and control at least one of (a) a temperature of the infusate infused into the patient through the insertion device in a downstream direction, (b) an infusion rate of the infusate, and (c) a volume of the infusate, in accordance with a temperature of the blood and infusate mixture upstream and adjacent an infusate exit location on the insertion device.

The controller may be adapted to control a temperature of the infusate in accordance with (1) a temperature of a blood and infusate mixture downstream relative to the infusate exit location of the insertion device, and (2) at least one of (a) the temperature of the infusate at least one of at and adjacent the exit location, (b) the temperature of the infusate upstream and adjacent the exit location, and (c) a core body temperature of the patient.

According to an exemplary embodiment of the present invention, an intravascular cooling catheter system may include a catheter having at least one temperature sensor or thermistor, at least one infusate reservoir or source, an infusion pump, and a controller or servomechanism. The catheter may include a longitudinal tubular member having a distal end, a proximal end, and at least one longitudinally extending lumen, and at least one temperature sensor or thermistor positioned on the outer surface of the catheter or within a lumen adjacent to or proximal to its distal end. Each temperature sensor may be electrically or functionally connected to the controller, which may also be electrically or functionally connected to the infusion pump. The outlet of the infusion pump may be in fluid communication with at least one lumen of the catheter.

A wire from each temperature sensor may extend through a lumen of the catheter and/or through the wall of the catheter.

A temperature sensor may be positioned to measure a patient's core temperature.

In another embodiment of the invention, the distal end of the catheter may be configured so that blood mixes with cooled infusate.

In another embodiment of the invention, a temperature sensor may be positioned distal to the distal end of the catheter to measure the temperature of a mixture of cooled infusate and blood (admixture temperature).

In another embodiment of the invention, the second temperature sensor may be positioned within a lumen of the catheter.

In another embodiment of the invention, one or more of the temperature sensors may be annular in shape.

In another embodiment of the invention, the organ cooled may be the brain.

In an intravascular cooling catheter system, an alarm may sound if the temperature of the mixture of infusate and blood reaches a target temperature, if reflux is detected, if the infusion rate of the infusate falls to zero, if the infusion rate of the infusate exceeds a predetermined maxima, and/or if the admixture hematocrit drops below a predetermined minima.

According to an exemplary embodiment of the present invention, an infusion method may include: a) infusing an infusate into a patient through an insertion device; b) at least one of measuring and calculating at least one parameter of a bodily fluid; and c) controlling at least one of (i) at least one parameter of the infusate, (ii) an infusion rate of the infusate through the insertion device, and (iii) a volume of the infusate passing through the insertion device, in accordance with at least one parameter of a blood and infusate mixture, downstream relative to an infusate exit location of the insertion device when the insertion device is placed in a blood vessel of the patient for infusion of the infusate, and in accordance with at least one of (a) the at least one parameter of the infusate at or adjacent the exit location, (b) the at least one parameter outside the insertion device upstream and adjacent the exit location, and (c) a core body temperature of the patient.

The method may include iteratively comparing the at least one parameter of the blood and infusate mixture downstream relative to the exit location to a target at least one parameter and decreasing at least one of the volume and infusion rate of infusate through the insertion device if the at least one parameter of the blood and infusate mixture downstream relative to the exit location falls below the target at least one parameter and increasing at least one of the volume and infusion rate of the infusate through the insertion device if the at least one parameter of the blood and infusate mixture downstream relative to the exit location is above the target at least one parameter.

The method may include iteratively comparing the at least one parameter upstream and adjacent the exit location to a predetermined minimum at least one parameter and reducing at least one of the volume and infusion rate of the infusate through the insertion device if the at least one parameter upstream and adjacent the exit location falls below the predetermined minimum at least one parameter.

The method may include iteratively comparing the at least one parameter of the blood and infusate mixture downstream relative to the exit location to a target at least one parameter and decreasing at least one of the volume and infusion rate of infusate through the insertion device if the at least one parameter of the blood and infusate mixture downstream relative to the exit location exceeds the target at least one parameter and increasing at least one of the volume and infusion rate of the infusate through the insertion device if the at least one parameter of the blood and infusate mixture downstream relative to the exit location falls below the target at least one parameter.

The method may include iteratively comparing the at least one parameter upstream and adjacent the exit location to a predetermined maximum at least one parameter and reducing at least one of the volume and infusion rate of the infusate through the insertion device if the at least one parameter upstream and adjacent the exit location exceeds the predetermined maximum at least one parameter.

Controlling at least one of (i) at least one parameter of the infusate, (ii) an infusion rate of the infusate through the insertion device, and (iii) a volume of the infusate passing through the insertion device, may include controlling at least one of (i) a temperature of the infusate, (ii) an infusion rate of the infusate through the insertion device, and (iii) a volume of the infusate passing into the patient, in accordance with a temperature of a blood and infusate mixture downstream relative to an infusate exit location of the insertion device when the insertion device is placed in a blood vessel of the patient for infusion of the infusate, and in accordance with at least one of (a) a temperature of the infusate at or adjacent the exit location, (b) a temperature upstream and adjacent the exit location, and (c) a core body temperature of the patient.

The method may include using temperature sensors to measure at least one of (a) the temperature of the blood and infusate mixture, (b) the temperature of the infusate at or adjacent the exit location, (c) the temperature outside the insertion device upstream and adjacent the exit location, and (d) the core body temperature.

The method may include calculating at least one of (a) the temperature of the infusate at or adjacent the exit location, (b) a dilution of the blood downstream relative to an infusate exit location of the insertion device, and (c) an admixture hematocrit, e.g., downstream relative to an infusate exit location of the insertion device.

The method may include calculating the dilution of the blood and the admixture hematocrit, e.g., downstream the exit location, using the equation (Hct)*(1−dF), where Hct is a base whole body hematocrit of the patient, dF is the dilution of the blood and is represented by the following equation dF=(infusion rate)/(infusion rate+X), wherein X represents the amount of blood per unit time at the core body temperature in the blood and infusate mixture and, e.g., when there is no reflux, is represented by the equation $$X = (\text{infusion rate}) \cdot (T_1 - T_2)/(T_4 - T_1)),$$

wherein $T_1$ is a temperature of the blood and infusate mixture downstream the exit location, $T_2$ is a temperature of the infusate at or adjacent the exit location, $T_3$ is temperature adjacent to and upstream the exit location, and $T_4$ is the core body temperature of the patient.

The calculation of dilution of the whole body hematocrit may also take into account the volume of infusate added to the patient's blood and the volume of the infusion fluid output by the patient, e.g., through urination.

The method may include iteratively comparing the temperature of the blood and infusate mixture downstream relative to the exit location to a target temperature and decreasing at least one of the volume and infusion rate of infusate through the insertion device if the temperature of the blood and infusate mixture downstream relative to the exit location falls one of (i) below the target temperature, and (ii) more than a predetermined amount below the target temperature, and increasing at least one of the volume and infusion rate of the infusate through the insertion device if the temperature of the blood and infusate mixture downstream relative to the exit location is above the target temperature.

The method may include iteratively comparing the temperature upstream and adjacent the exit location to a predetermined minimum temperature and reducing at least one of the volume and infusion rate of the infusate through the insertion device if the temperature upstream and adjacent the exit location falls one of (i) below the predetermined minimum temperature, and (ii) more than a predetermined amount below the predetermined minimum temperature. The predetermined minimum temperature may correspond to the core body temperature.

The at least one of (i) the at least one parameter of the infusate, (ii) the infusion rate of the infusate through the insertion device, and (iii) the volume of the infusate passing through the insertion device may be controlled in the controlling step such that the blood and infusate mixture reaches or falls below a predetermined target temperature.

According to an exemplary embodiment of the present invention, an infusion method may include: a) infusing an infusate into a patient through an insertion device; b) measuring at least one parameter of a bodily fluid; and c) controlling at least one of (i) at least one parameter of the infusate, (ii) an infusion rate of the infusate through the insertion device, and (iii) a volume of the infusate passing into the patient, in accordance with the at least one parameter upstream and adjacent the exit location. Upstream and adjacent the exit location may be about 0.2 cm to about 5 cm upstream the exit location.

The method may include iteratively comparing the at least one parameter upstream and adjacent the exit location to a predetermined minimum at least one parameter and reducing at least one of the volume and infusion rate of the infusate through the insertion device if the at least one parameter upstream and adjacent the exit location falls below the predetermined minimum at least one parameter.

The at least one parameter of the bodily fluid may be a temperature of the bodily fluid and the controlling step (b) above may include controlling at least one of (i) a temperature of the infusate, (ii) an infusion rate of the infusate through the insertion device, and (iii) a volume of the infusate passing into the patient, in accordance with a temperature outside the insertion device upstream and adjacent the exit location. The predetermined minimum at least one parameter may correspond to a core body temperature of the patient.

The method may include increasing the infusion rate of the infusate until reflux is achieved.

The system may be a patient, the system fluid may be the patient's blood, and the insertion device may be inserted into a blood vessel of the patient, and the method may further include: increasing the infusion rate of the infusate until reflux is achieved, and calculating at least one of (i) a native vessel flow rate in the blood vessel, (ii) a dilution factor of the blood in the blood vessel, (iii) an admixture hematocrit, i.e., a hematocrit of the blood and infusate mixture in the blood vessel, and (iv) a temperature of the blood and infusate mixture in the blood vessel in accordance with a determination as to when reflux occurs.

According to an exemplary embodiment of the present invention, an infusion method may include: a) infusing an infusate into a patient through an insertion device; and b) controlling at least one of (i) an infusion rate of the infusate through the insertion device, and (ii) a volume of the infusate passing into the patient in accordance with an admixture hematocrit, e.g., downstream an infusate exit location on the insertion device.

The method may include iteratively comparing the admixture hematocrit, e.g., downstream the exit location, to a minimum predetermined hematocrit and reducing at least one of the volume and infusion rate of the infusate through the insertion device if the admixture hematocrit falls below the minimum predetermined hematocrit. The method may further include calculating the admixture hematocrit using the equation $(Hct)*(1-dF)$, as detailed above.

Some of the example embodiments set forth above are directed to the measurement and/or calculation of temperature and/or hematocrit and the use of that temperature and/or hematocrit information to control tissue or organ cooling procedures. It should be appreciated that in other embodiments and as set forth below other characteristics or properties of blood, blood flow, infusate, and/or infusate flow may be measured or sensed to control tissue or organ cooling procedures and/or the delivery of infusate. These embodiments encompass and/or are applicable to characteristics or properties that may be sensed or measured to differentiate infusate from blood or to otherwise facilitate determining the rate of blood flow or infusate flow and/or reflux, including, but not limited to, endogenous and exogenous tracers, etc. For example, sensors may determine a physiological parameter of the blood and infusate mixture that is measurable, stable, and may have first pass viability, e.g., temperature, pH, oxygen content, salt content, drug content, tracer content, etc., so that infusate blood flow, and/or reflux may be determined.

According to an exemplary embodiment of the present invention, an infusion method may include: a) infusing an infusate into a patient through an insertion device inserted in the patient's blood vessel; b) at least one of measuring and calculating the patient's nvFR in the blood vessel; and c) controlling at least one of (i) at least one parameter of the infusate, (ii) an infusion rate of the infusate through the insertion device, and (iii) a volume of the infusate passing through the insertion device, in accordance with the patient's nvFR.

The method may include decreasing the temperature of the infusate or increasing the infusion rate or volume of the infusate if a rate of change of the nvFR is below a predetermined value.

According to an exemplary embodiment of the present invention, an infusion method may include: a) infusing an infusate into a patient through an insertion device in a downstream direction; and b) controlling at least one of (i) at least one parameter of the infusate, (ii) an infusion rate of the infusate through the insertion device, and (iii) a volume of the infusate passing through the insertion device, in accordance with a flow rate of a bodily fluid in the downstream direction.

A device according to an exemplary embodiment of the present invention may include: i) an insertion device adapted to fluidicly communicate with a source of an infusate and to be placed in a blood vessel; and ii) a controller adapted to control at least one of (a) a temperature of the infusate, (b) an infusion rate of the infusate through the insertion device into the blood vessel, and (c) a volume of the infusate passing through the insertion device in a downstream direction into the blood vessel, in accordance a native vessel blood flow rate in the blood vessel.

In an exemplary embodiment of the present invention, the infusate may include Na+ ions at a higher concentration than found in the patient's blood. Sensors on the wire or infusion device may be configured to sense Na+.

According to an exemplary embodiment of the present invention, a delivery device may include: a) an insertion device adapted to fluidicly communicate with a source of an infusate, e.g., a fluid or a gas or any material flowable in the system in a first direction, and inserted into a system filled with a flowing material, e.g., at least one of a fluid and gas; b) a sensor located exterior to an internal lumen of the insertion device and a distance away from an infusate exit location of the insertion device along a second direction opposite the first direction; and c) a controller adapted to receive signals from the sensor indicative of at least one parameter of at least one of the flowing material in the system to control at least one of (i) at least one parameter of the infusate, (ii) an infusion rate of the infusate through the insertion device, and (iii) a volume of the infusate passing through the insertion device in accordance with the signals from the sensor.

According to an exemplary embodiment of the present invention, an infusion method may include: a) infusing an infusate into a system through an insertion device in a first direction, said system having at least one of a fluid and gas flowing therein in the first direction; b) at least one of measuring and calculating at least one parameter of the at least one of a fluid and gas; and c) controlling at least one of (i) at least one parameter of the infusate, (ii) an infusion rate of the infusate through the insertion device, and (iii) a volume of the infusate passing through the insertion device, in accordance with at least one parameter of a mixture of the infusate and the at least one of a fluid and gas at a position spaced away from an infusate exit location of the insertion device along the first direction when the insertion device is placed in the system for infusion of the infusate, and in accordance with at least one of (a) the at least one parameter of the infusate at the exit location, (b) the at least one parameter outside the insertion device adjacent the exit location and spaced a distance away from the exit location in a second direction opposite the first direction, and (c) an average value of a parameter of the at least one of a fluid and gas in the system.

According to an exemplary embodiment of the present invention, an infusion method may include: a) infusing an infusate into a system through an insertion device in a first direction, said system having at least one of a fluid and gas flowing therein in the first direction; b) at least one of measuring and calculating at least one parameter of the at least one of a fluid and gas; and c) controlling at least one of (i) at least one parameter of the infusate, (ii) an infusion rate of the infusate through the insertion device, and (iii) a volume of the infusate passing through the insertion device, in accordance with at least one parameter of a mixture of the infusate and the at least one of a fluid and gas at a position spaced away from an infusate exit location of the insertion device along the first direction when the insertion device is placed in the system for infusion of the infusate, and in accordance with a rate of flow of the at least one of a fluid and gas.

One or more of the temperature sensors described herein may be replaced by, for example, inline gas analyzers, including, but not limited to, (a) an opto-chemical pH detector that changes color in response to ambient pH readings, (b) an opto-chemical $PCO_2$ sensor that changes color in response to the $PCO_2$, or (c) a Clark oxygen electrode (such as those believed to be available from companies such as Biomedical Sensors, Ltd.). Sensors may detect methylene blue or neuroprotective agents as well. Modifications of the algorithms discussed below may allow these tracers to be used to obtain a similar result. The concept, method, and algorithm would be congruent in embodiments using tracers other than temperature.

Delivery systems may be applied to deliver agents such as chemotherapeutic agents, where the extraction fraction is so great that it is desired to administer such agents in as dilute a form as possible, e.g., admixed with a large proportion of physiologically acceptable solution. The tracer may be administered in the infusate, and the dilution factor, discussed below, may be monitored.

In an exemplary embodiment, the insertion device may include a Doppler ultrasound device, e.g., as disclosed by U.S. Pat. No. 7,211,045, herein incorporated in its entirety by reference thereto. The Doppler ultrasound device may be adapted to measure the nvFR and/or the admixture flow rate when the insertion device is placed in the patient's blood vessel. Doppler measurements may also be taken to determine the relative flow adjacent the distal portion of a catheter to indicate the reflux of infusate/blood admixture.

Alternatively, if it is assumed that the temperature of the infusate and the core temperature are known, that the temperature is a weighted mean, and the target temperature is the temperature of the admixture, the mean velocity is used as a measure of change in flow. Thus, assumptions are made, and reflux is perceived proportional to a change in velocity.

An aspect hereof is to adjust the infusion rate to reach an equilibrium state so that the blood and infusate mixture reaches or falls below a target temperature.

Example embodiments of the present invention are described in more detail below with reference to the appended Figures. The foregoing description and examples have been set forth merely as illustrative and are not intended as being limiting. Each of the disclosed aspects and embodiments may be considered individually or in combination with other aspects, embodiments, and variations thereof. The steps of the methods described herein are not confined to any particular order of performance.

DETAILED DESCRIPTION

Figure 1:
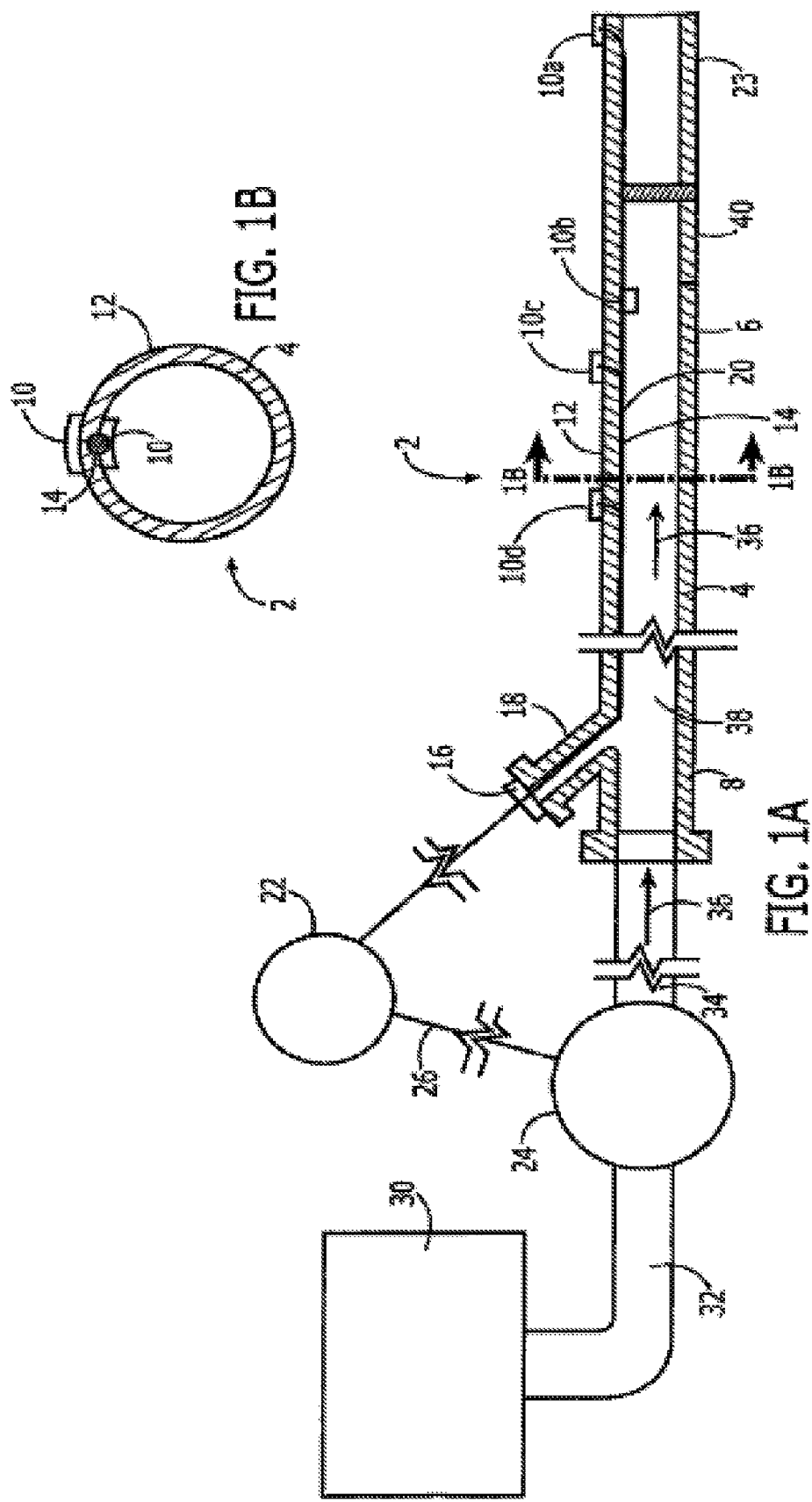
FIG. 1A is a schematic representation of a cooling system according to an exemplary embodiment of the present invention.
FIG. 1B is a cross-sectional view along the line 1B-1B in FIG. 1A.

FIG. 1A is a schematic representation of a catheter 2 according to an exemplary embodiment of the present invention including a longitudinally extending tubular member 4 having a distal catheter section 6 and a proximal catheter section 8. The catheter 2 is inserted into a patient distal catheter section 6 first. Distal catheter section 6 has one or more sensors 10a, 10b, 10c, 10d, such as temperature sensors, e.g., thermistors, affixed to or embedded in the outer surface 12 and/or inner surface 20 of tubular member 4. Each sensor 10a, 10b, 10c, 10d may have a proximally extending wire 14 that extends into and through a lumen 38 of catheter 2 and connects through plug 16 in a manifold 18 to a microprocessor, servomechanism, or controller 22. Alternatively, each wire 14 may extend through a wall of the catheter 2 or sensors 10a, 10b, 10c, 10d may be wireless. FIG. 1b is a cross-sectional view of catheter 2 taken along the line 1B-1B. Controller 22 is able to adjust infusion rate, e.g., with a tolerance of e.g., about 1 cc/min., to maintain the measured temperature at the distal catheter tip 23 via, e.g., sensor 10a, from, e.g., about −10° to about 40° C., for a predetermined period of time. For safety reasons, the length of the predetermined period of time may be controlled, e.g., so as to so as to prevent a predetermined body temperature drop, e.g., of 1 to 1.5 degrees Celcius, and/or so as to prevent a predetermined whole body hematocrit drop, e.g., to below 25, and/or so as to prevent against a fluid overload in the patient.

Catheter distal section 6 includes an infusate exit region or area 40, including, for example, outlets, slits, and/or perforations (hereinafter "the outlets") to facilitate the admixture of infusate with blood. The outlets may be designed to generate turbulent flow of the infusate, which further facilitates the admixture of infusate with blood, without significantly increasing the risk of vascular damage. The design of the outlets assures that the cooled infusate and blood are totally mixed by the time the admixture flows past sensor 10a in FIG. 1. For example, the outlets may have a spiral or screw-like pattern. Further, the outlets may be oriented perpendicular to a longitudinal axis of the catheter 2 and the direction of nvFR such as, but not limited to, ninety degrees plus or minus 25 degrees in relation to the longitudinal axis. Also, a grid or screen in the inlet with many fine holes or a larger number of smaller orifices in the catheter distal section 6 may be used to break up laminar flow so as to increase turbulence and mixing.

An infusion pump 24 is operatively connected to controller 22, for example, through one or more wires 26. Any infusate pump, for example, a blood pump with a wide dynamic range, e.g., from about 2 cc/min to about 360 cc/min may be used for pump 24. Cooled infusate in a heat exchanger, such as a temperature controlled reservoir or cooler 30, is drawn into pump 24 through inlet 32 and expelled through outlet 34 in the direction of arrows 36 to the at least one lumen 38 in catheter 2, for example, at a rate of 30 mL/min and a temperature of 0° C. (273K). The temperature of the infusate is controlled by the controller 22 by adjusting the temperature in the cooler 30. Alternatively, the temperature of the infusate infused into a patient may be controlled by using both a heated source of infusate, heated by a heat exchanger, such as heater 31, in combination with the cooled source provided by the cooler 30, as illustrated in FIG. 2.

Figure 2:
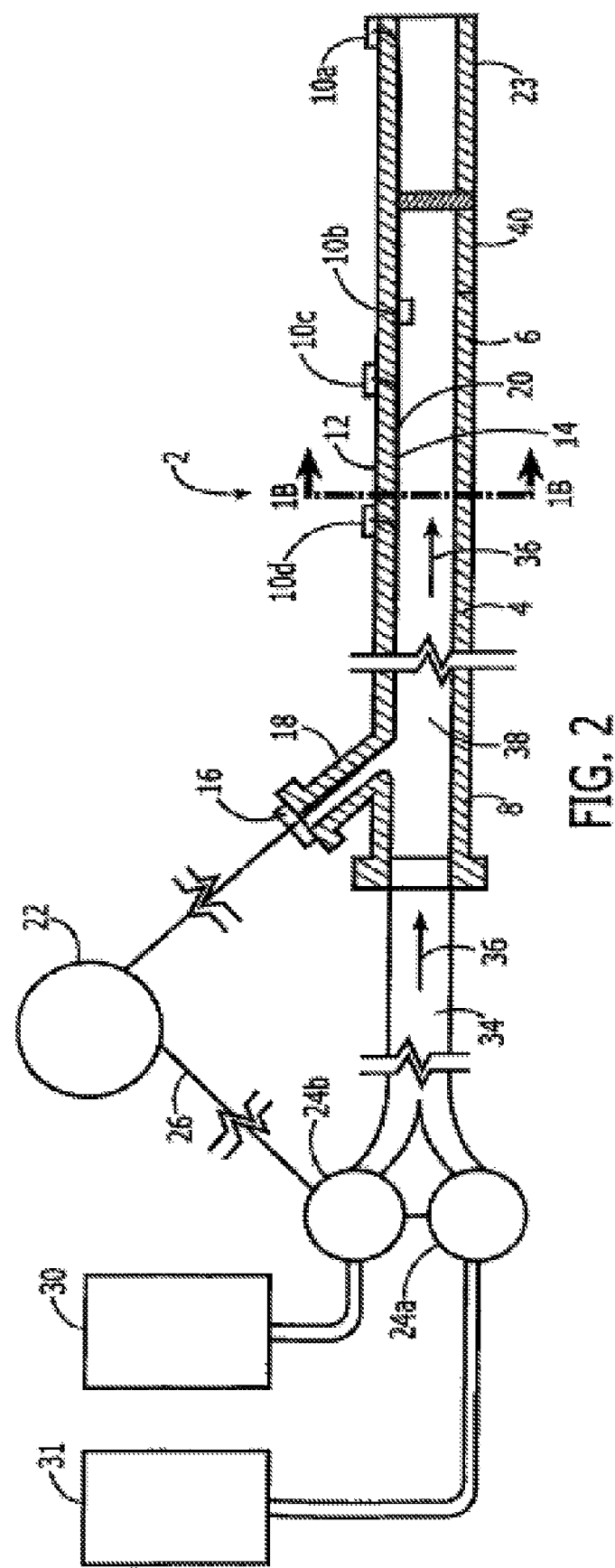
FIG. 2 is a schematic representation of a cooling system according to an exemplary embodiment of the present invention.

As illustrated in FIG. 2, heater 31, controlled by pump 24a, is used in combination with cooler 30, controlled by pump 24b, to determine the ultimate temperature of the infusate infused into the patient. Controller 22 determines the relative proportion of infusate pumped from the cooler 30 and the infusate pumped from the heater 31. Alternatively, pumps 24a, 24b may be replaced with two pressurized reservoirs including infusate, for example, at different temperatures and controller 22 may control a parameter of the infusate, e.g., its temperature, by selectively opening up the reservoirs, for example, using valves, to different degrees.

Sensors 10a, 10b, 10c, 10d are embedded in catheter 2 or affixed to catheter outer surface 12 or catheter inner surface 20 by any physiologically acceptable adhesive or by a physical affixation such as a wire or strap. Sensors 10a, 10b, 10c, 10d measure a physiological parameter that is measurable, and stable, e.g., temperature, pH, oxygen content, salts, drugs, and some tracers. The iterations of the exemplary device and method discussed below use, as an example, temperature sensors, however, congruent calculations, algorithms, and design characteristics may be used with any other of the above-mentioned parameters with only slight modification. Further, while the exemplary device discussed below may control the temperature of the infusate, other parameters of the infusate, e.g., temperature, pH, oxygen content, salt content, drug content, tracer content, etc., may be controlled in accordance with the measured parameter of the blood and infusate mixture. In other words, the measured parameter of the bodily fluid does not necessarily correspond to the parameter of the infusate controlled by the controller 22.

Sensor 10a measures a parameter, such as temperature ($T_1$), of the blood and infusate mixture downstream or distal the exit region 40. Sensor 10a may be placed far enough away from the exit region 40, e.g., a distance of about 1 to 10 cm or about ten times the diameter of the blood vessel in which the catheter 2 is positioned, so as to assure that the measurement being taken is of a fully mixed blood and infusate admixture. Sensor 10b measures a parameter, such as the temperature ($T_2$), of the cooled infusate at or adjacent the exit region 40 of the infusate from the catheter 2. Sensor 10c measures a parameter, such as the temperature ($T_3$), at a position adjacent to and upstream, e.g., about 0.2 cm to about 5 cm, from the exit region 40. As detailed below, sensor 10c is positioned close enough to the exit region 40 to detect reflux of the infusate. Sensor 10d measures a parameter, such as temperature ($T_4$), at a proximal position along the catheter 2. Sensor 10d may be positioned proximal enough along the catheter 2 to assure, for example, that a core body temperature of the patient is being measured.

Sensors 10a, 10b, 10c, 10d may each include multiple sensors, for example, deployed annularly to detect an annular space around catheter 2. Each of temperatures $T_1$ to $T_4$ may be measured by two or more sensors, in which case an average value for a particular temperature may be determined or measured by averaging the measurements from each of these sensors. The number of sensors used and the number of temperature points measured may depend upon factors such as the particular application and/or the desired functionality. While four temperature points $T_1$ to $T_4$ are mentioned above, temperatures may be measured at more or less points. Combinations of two or three of $T_1$ to $T_4$ may be measured, dependent upon the particular application and/or the desired functionality. Only a single temperature point, such as $T_1$ or $T_3$, may be used for certain applications. Further, as detailed below, rather than or in addition to measuring temperature or other parameters at various points along the catheter, the controller 22 may calculate or estimate these values.

Sensor 10a, 10b, 10c, 10d may measure a parameter in addition to or other than temperature. For example, sensors 10a, 10b, 10c, 10d may measure pressure and may include a transducer or diaphragm, optionally with a fiber optic cable. For representative examples of pressure and/or temperature sensor technology, see, for example, U.S. Pat. Nos. 4,487,206, 4,641,654, 5,427,114, 5,456,251, 5,325,865, 5,647,847, 5,866,821, and 5,899,927, each of which is expressly incorporated herein in its entirety by reference thereto. In addition to measuring backflow of infusate, pressure measurement may be of interest in and of itself. Flow and pressure greater than the desired range may lead to brain injury, and flow and pressure less than the desired range may be insufficient to achieve organ cooling.

Different systems may have different numbers of sensors, in terms of placement and function. A single sensor or multiple sensors can be used in place of an annular sensor. Only a single sensor at only one of the locations described herein may be used. Also, the particular type or number of sensors is not critical. A patient's core temperature can be measured as described above, or it could be measured elsewhere in a patient's body or even calculated as a constant reference point. The temperature sensors can be capable of sensing temperatures, for example, in the range of from about 0° to about 50° C.

The information from the sensors 10a, 10b, 10c, 10d is transmitted to controller 22, which may send signals to pumps 24, 24a, and 24b to adjust flow and temperature of infusate according to a control scheme. For example, controller 22 can employ a feedback loop so as to iteratively measure at a predetermined rate a parameter, such as the temperature ($T_1$), of the infusate and blood mixture downstream of the exit region 40 and compare it to a predetermined target parameter, for example, a predetermined target temperature, e.g., 33° C. or 306K. The controller 22 instructs at least one of pumps 24, 24a, 24b to continue to increase at least one of a infusion rate and volume of infusate delivered to the patient and/or instruct cooler 30 and/or heater 31 to continue to decrease a temperature of the infusate until $T_1$ reaches or falls below the target temperature. The target temperature may be chosen by a user, e.g., so as to achieve a target degree of hypothermia. For example, the target temperature may be set to between 33° C. and 36° C. to achieve a mild hypothermia, to between 29° C. and 32° C. to achieve a moderate hypothermia, or to below 28° C. to achieve severe hypothermia.

Controller 22 can also employ a feedback loop so as to iteratively measure a parameter, such as the temperature, of either the blood or blood and infusate mixture using sensor 10c. Controller 22 is programmed to look for a change in the parameter detected by sensor 10c, which is reflective of a reflux condition, and upon detection of reflux instruct the pump 24 to decrease the infusion rate and/or volume of infusate delivered to the patient.

Controller 22 can also employ a feedback loop so as to iteratively measure a patient's nvFR. Controller 22 may be programmed to increase or decrease flow of infusate or the temperature of the infusate based on the nvFR, e.g., depending on a rate of change of the nvFR. For example, if the nvFR is not decreasing at a fast enough rate the controller 22 may be programmed to increase the flow rate of cooled infusate or decrease the temperature of the infusate.

The above discussion regarding the use of sensors 10a, 10b, 10c, 10d assumes that catheter 2 is positioned in a blood vessel in the direction of blood flow. However, catheter 2 can also be positioned in a blood vessel in a direction opposite the direction of blood flow. In which case, the roles of sensors 10a and 10c can be switched, i.e., sensor 10a can be used to detect reflux and sensor 10c can be used to detect a temperature of the infusate and blood mixture.

As the temperature of tissue or an organ in a patient falls, the patient's metabolism also falls, and this fall in metabolism decreases blood flow. Metabolism in a human patient substantially ceases in a patient when the temperature of the patient, or at least a particular portion of the patient, approaches 20° C. With regard to the brain, blood flow through a carotid artery is approximately 5 cc/sec (or 300 cc/min) when the temperature of the brain is 38° C. However, the rate of blood flow through the carotid artery quickly falls to near zero as the temperature of the brain reaches 20° C. Once the temperature of the brain reaches 20° C. due to the cooled infusate, the volume of cooled infusate needed to cool the brain also is reduced to near zero. The blood can be cooled to below 20° C. so as to stop all blood flow through the carotid artery. In a situation where the brain is infused with cooled infusate to cool the brain, cooled infusate will be refluxed back along the infusate catheter as the rate of flow of infusate exceeds the flow necessary for cooling. Reflux can start even before the blood reaches 20° C. As indicated above, sensor 10o is positioned on catheter 2 so as to detect such a reflux condition.

Figure 3A:
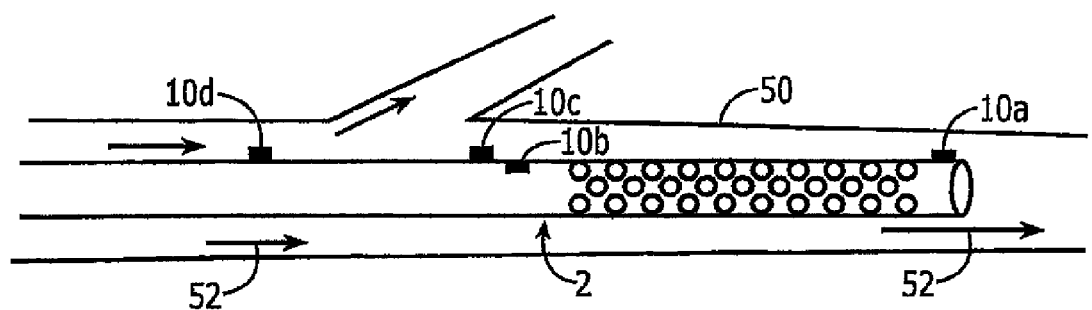
FIG. 3A is a schematic representation of a catheter according to an exemplary embodiment of the present invention positioned in a patient's carotid artery.
Figure 3B:
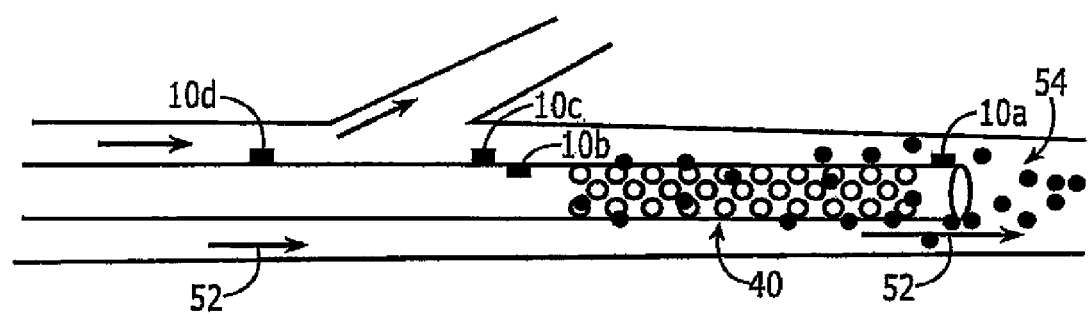
FIG. 3B is a schematic representation of the catheter illustrated in FIG. 3A infusing an infusate into the patient's carotid artery.
Figure 3C:
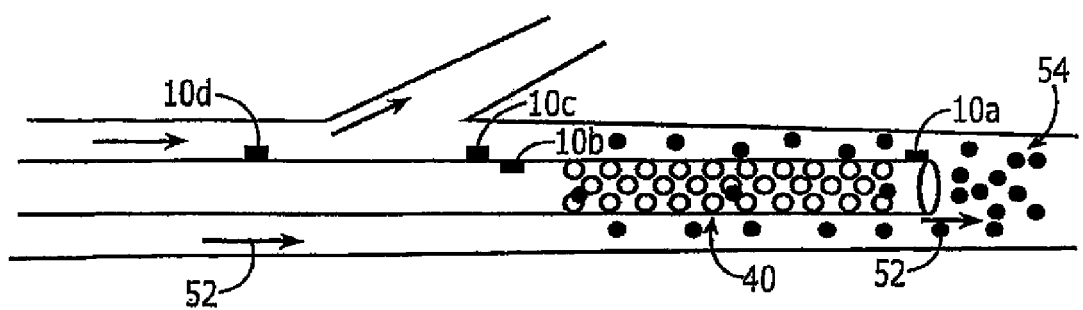
FIG. 3C is a schematic representation of the catheter illustrated in FIG. 3A infusing an infusate into the patient's carotid artery, the patient's free flow contribution reduced compared to that in FIG. 3B.
Figure 3D:
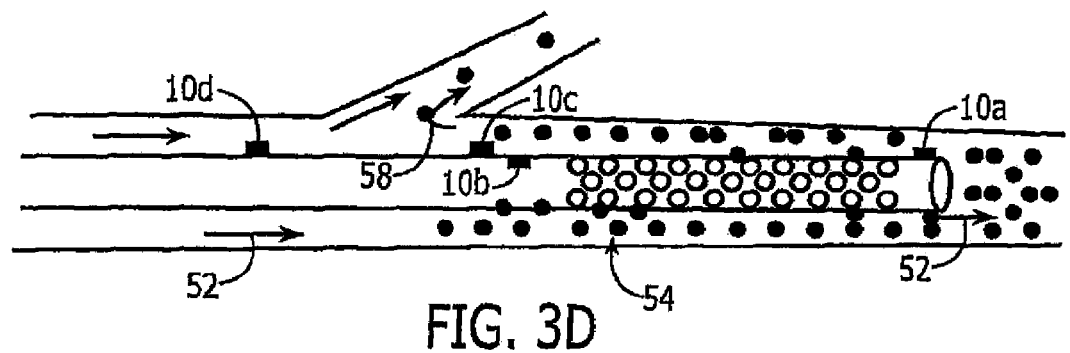
FIG. 3D is a schematic representation of the catheter illustrated in FIG. 3A surrounded by a reflux of blood and infusate.

Reflux of the infusate and blood mixture is illustrated in FIGS. 3A to 3D, 4A to 4C, and 5A to 5C. As can be seen in FIGS. 3A to 3D, catheter 2 may be positioned in a patient's carotid artery 50. For reference, the left side of artery 50, as illustrated in FIGS. 3A to 3D, is closer to the patient's heart. FIG. 3A represents an initial positioning where the patient's blood is flowing downstream through the carotid artery 50 in the direction of arrows 52, the temperature of which blood is sensed by sensor 10d. A cooled infusate travels through catheter 2, exits the catheter 2 through exit region 40, and enters carotid artery 50, as illustrated in FIG. 3B, and the mixture of blood and infusate 54 perfuses downstream toward the patient's brain in the direction of arrow 52. Note that for clarity only one of the holes in the exit region 40 of catheter 2 is shown in FIG. 1, however, as illustrated in FIGS. 3A to 3D and 4A to 4C, this region may have multiple holes. Flow to the brain begins to decrease, as illustrated by the smaller arrow 52 in FIG. 3C, and the infusate and blood mixture 54 eventually refluxes and begins to flow past the exit region 40 in a direction opposite the flow of infusate in the catheter 2, e.g., upstream in the carotid artery 50, as reflected by arrow 58 in FIG. 3D. Sensor 10c senses a temperature of fluid flow adjacent the exit region 40. When there is reflux of the infusate and blood mixture 54, a controller, such as that illustrated in FIG. 1, recognizes this condition by iteratively looking, for example, at a predetermined time interval, for a drop in the temperature measured by sensor 10c and sends a signal to a pump, such as that illustrated in FIG. 1, to cause the controller to slow down or stop the infusion of infusate. Reflux may be measured during infusion and/or after the infusion of a bolus of infusate. For example, the infusion may be performed continuously or non-continuously, e.g., by periodically injecting boluses. For non-continuous infusion, reflux may be periodically measured after each injection or after a predetermined number of injections.

Figure 4A:
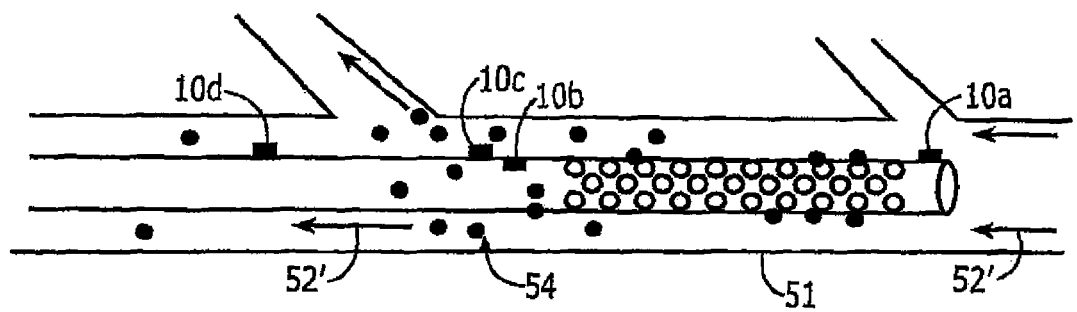
FIG. 4A is a schematic representation of a catheter according to an exemplary embodiment of the present invention positioned in a patient's femoral artery.
Figure 4B:
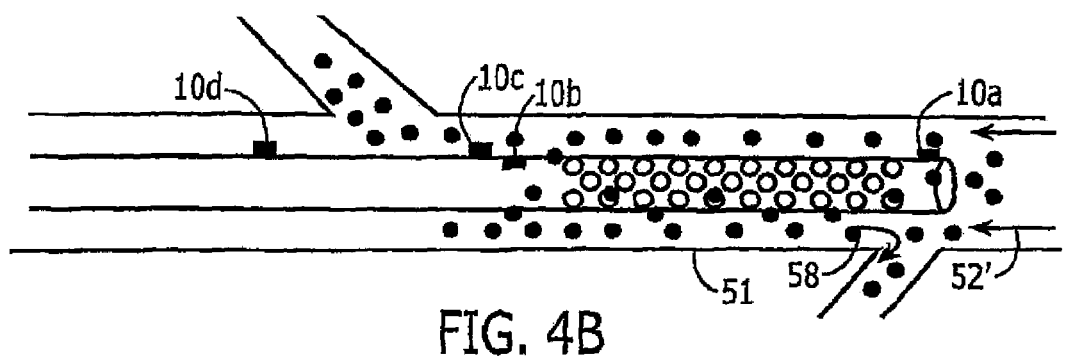
FIG. 4B is a schematic representation of the catheter of FIG. 4A with a tip of the catheter exposed to reflux of the blood and infusate.

Catheter 2 may also be positioned in a retrograde manner, for example, in the femoral artery 51, as illustrated in FIGS. 4A and 4B. For reference, the right side of catheter 2 in FIGS. 4A and 4B is closer to the patient's heart. Infusate, passing through the catheter 2 and exit region 40, mixes with blood and the mixture 54 flows in the direction of arrow 52' away from sensor 10a and towards sensor 10c. Flow towards the foot begins to slow and the blood and infusate mixture 54 eventually refluxes in the direction of arrow 58' past sensor 10a. When there is reflux of the infusate and blood mixture 54, a controller, such as that illustrated in FIG. 1, recognizes this condition by iteratively looking, for example, at a predetermined time interval, for a drop in the temperature measured by sensor 10a and sends a signal to a pump, such as that illustrated in FIG. 1, to cause the controller to slow down or stop the infusion of infusate.

The controller may be adapted to look to different sensors for different signals depending on where the catheter 2 is positioned in the patient. For example, in the situation illustrated in FIGS. 3A to 3D, when the catheter is positioned in the carotid artery 50 and the direction of infusate flow through the catheter 2 is the same as the direction of blood flow in the carotid artery 50 prior to reflux, the controller checks sensor 10c for a reflux condition, whereas when the catheter 2 is positioned in the femoral artery 51, as illustrated in FIGS. 4A and 4B, and the flow of infusate through the catheter 2 is opposite that of the blood flow in the femoral artery 51 prior to reflux, the controller is adapted to look to sensor 10a to detect a reflux condition. Similarly, if the catheter 2 in FIGS. 3A to 3D was inserted retrograde, i.e., flipped 180 degrees such that the exit region 40 was closer to the left side of the figure, and flow of infusate through the catheter 2 was in a direction opposite to the direction of blood flow through the carotid artery 50 before reflux, the controller may be adapted to look to sensor 10a to detect a reflux condition. Given that the function of one or more sensors depends on the positioning of the catheter 2 in the patient, the controller may accept input from a user indicating a desired mode of controller operation specific to the particular catheter positioning in the patient's body.

Figure 5A:
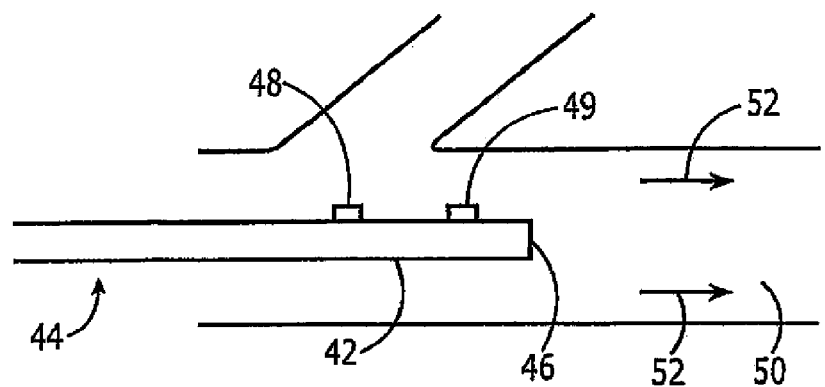
FIG. 5A is a schematic representation of a catheter according to an exemplary embodiment of the present invention positioned in a patient's carotid artery.
Figure 5B:
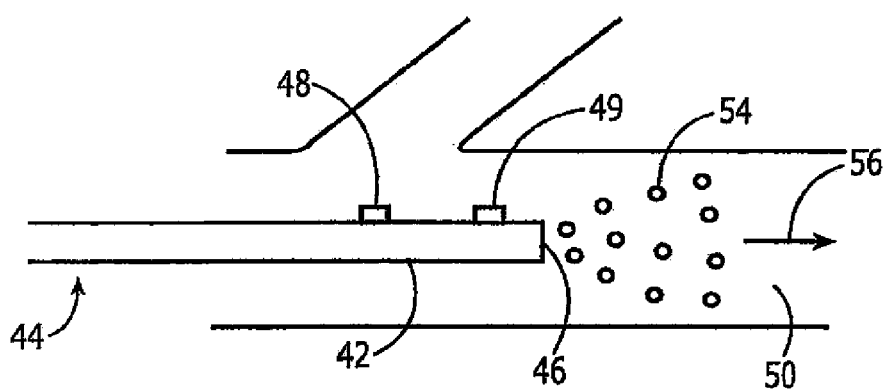
FIG. 5B is a schematic representation of the catheter illustrated in FIG. 5A infusing an infusate into the patient's carotid artery.
Figure 5C:
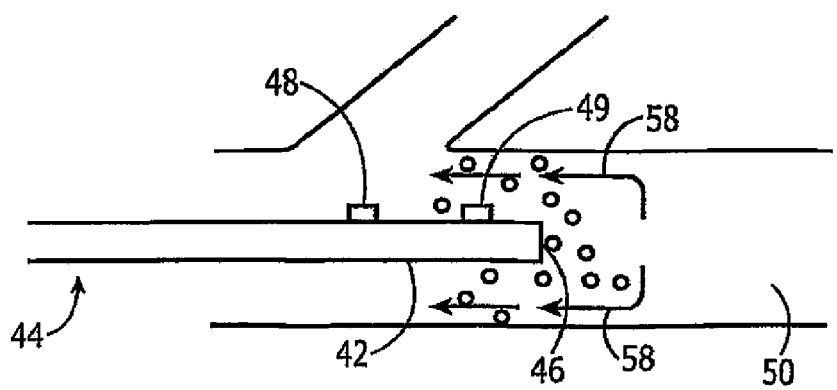
FIG. 5C is a schematic representation of the catheter illustrated in FIG. 5A surrounded by a reflux of blood and infusate.

FIGS. 5A to 5C illustrate an exemplary embodiment of an insertion device 44, such as a needle or catheter, having a distal opening 46 and temperature sensors 48 and 49, positioned in a patient's carotid artery 50. FIG. 5A represents an initial positioning where the patient's blood is flowing downstream through the carotid artery 50 in the direction of arrows 52, the temperature of which blood is sensed by sensor 48. As illustrated in FIG. 5B, cooled infusate enters carotid artery 50 through distal opening 46 and a mixture of infusate and blood 54 perfuses downstream in the direction of arrow 56 toward the patient's brain. Then, as or after flow to the brain decreases, the infusate and blood mixture 54 refluxes and begins to flow upstream, as reflected by arrows 58 in FIG. 5C. Sensor 49 senses a temperature of fluid flow adjacent to a distal portion 42 of insertion device 44. When there is reflux of the infusate and blood mixture 54, a controller, such as that illustrated in FIG. 1, recognizes this condition by iteratively looking, for example, at a predetermined time interval, for a drop in the temperature measured by sensor 49 and sends a signal to a pump, such as that illustrated in FIG. 1, to cause the controller to slow down or stop the infusion of infusate.

Given the elongate nature of the catheter 2 used to deliver the infusate, the infusate can warm up in transit between the pump 24 and the exit region 40 on the catheter 2. The temperature of the infusate exiting the catheter 2 can be measured using, for example, sensor 10b or can be calculated by the controller 22 taking into account this warming of the infusate.

The temperature of the cold infusate as it exits from the catheter 2 may also be calculated using the general thermodynamic equation $\Delta Q=mc(\Delta T)$ as generally discussed on page 927 of "Locally induced hypothermia for treatment of acute ischemic stroke: a physical feasibility study," Neuroradiology (2004) 46:923-934, Epub 2004 Nov. 17, herein expressly incorporated in its entirety by reference thereto, wherein $\Delta Q$ represents a change in heat of a given material being measured, m represents the mass of the material, c represents the specific heat property of the material, and $\Delta T$ is the change in temperature of the material.

As detailed below, the general thermodynamic equation $\Delta Q=mc(\Delta T)$ can be used to solve for the native blood contribution (X), which equation can be transformed to solve for the temperature of the infusate as it exits the catheter.

When the blood and infusate are mixed, the general thermodynamic equation $\Delta Q=mc(\Delta T)$ becomes:

$$\Delta Q_B + \Delta Q_I = m_B c_B \Delta T_B + m_I c_I \Delta T_I$$

where the subscript B denotes blood and I denotes infusate. Setting the heat capacities of the blood and infusate equal to 1, on the assumption that these fluids have heat capacities similar to water, and setting $\Delta Q_I = -\Delta Q_B$, on the assumption that no heat leaks into the admixture from the surrounding tissue, i.e., energy is conserved, the above equation can be transformed to $0 = v_B \Delta T_B + v_I \Delta T_I$, where $v_B$ is volume of the blood, $T_A$ is the admixture temperature (assuming a uniform admixture temperature), $\Delta T_B = T_A - T_B$ and represents the change in blood temperature, and $\Delta T_I = T_A - T_I$, which represents the temperature change in the infusate. Substituting the relevant parameters of, for example, catheter 2 (FIG. 1A) into the equation $0 = v_B \Delta T_B + v_I \Delta T_I$ including $T_1$ (temperature of blood and infusate admixture), $T_4$ (overall body blood temperature), and $T_2$ (infusate temperature) for $T_A$, $T_B$, and $T_I$, respectively, and replacing $v_B$ with the native blood contribution (X) multiplied by time (t) yields the following equation:

$$0 = X \cdot t \cdot (T_4 - T_1) + IR \cdot t \cdot (T_1 - T_2)$$

Solving for native blood contribution (X) and dividing out time (t) yields:

$$X = IR \cdot \frac{T_2 - T_1}{T_1 - T_4}$$

The behavior described by the equation above for native blood flow contribution (X) also applies to other cases in which two fluids possess a property in different amounts and mixing is complete. For example, the infusate may carry a concentration of sodium ions that differs from the sodium concentration in native blood. Generalizing the sensors in FIG. 1 to measure any property P, the concentrations may be defined as:

$P_1 = [Na^+]$ of admixture (meq/L);

$P_2 = [Na^+]$ of infusate (meq/L);

$P_3 =$ Reflux $[Na^+]$(meq/L);

$P_4 =$ Overall blood $[Na^+]$(meq/L);

IR=Infusion Rate (cc/s); and

X=Native Blood Contribution (cc/s).

The sodium concentration of the admixture ($P_1$) is the sum of the amount of sodium in the blood and infusate, divided by the total volume of the admixture. The equation for sodium concentration of the admixture ($P_1$) is as follows:

$$P_1 = \frac{P_2 \cdot IR \cdot t + P_4 \cdot X \cdot t}{IR \cdot t + X \cdot t}$$

where t is time. Note that the amount of sodium is expressed in the same form as the amount of heat described above, i.e., as the product of concentration, infusion rate and time. Dividing out time and solving for X, the equation above becomes:

$$X = IR \cdot \frac{P_2 - P_1}{P_1 - P_4}$$

which is a generalized form of the equation $$X = IR \cdot \frac{T_2 - T_1}{T_1 - T_4}$$

above.

So as to provide a sufficiently low temperature of the infusate upon exit of the catheter, the catheter can include an insulating sleeve or other coating so as to minimize heat transfer from the blood or surrounding tissue to the cooled infusate. Further, the catheter can be delivered into the patient through a guide catheter, in which case the guide catheter itself and an insulator in the guide catheter serve to insulate the catheter and maintain the temperature of the cooled infusate.

Figure 6:
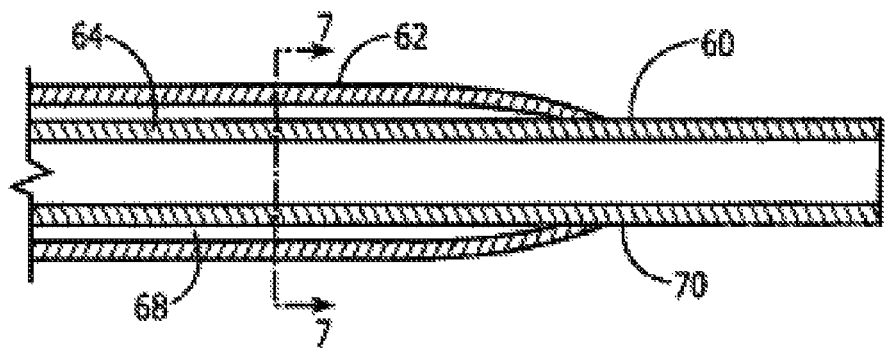
FIG. 6 is a longitudinal cross-sectional view of an insulated catheter according to an exemplary embodiment of the present invention.
Figure 7:
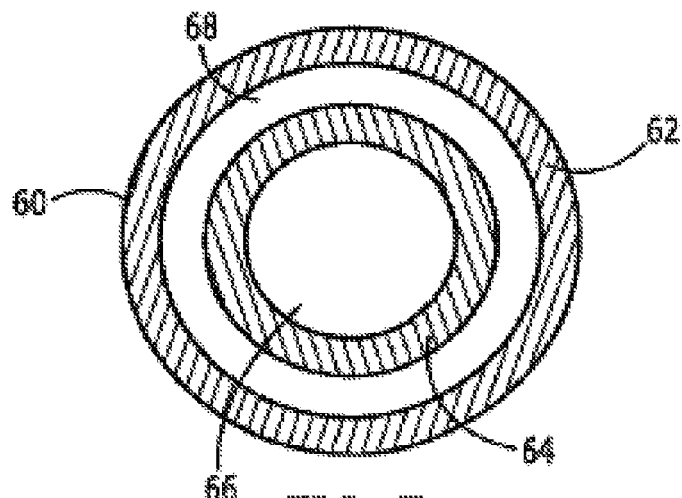
FIG. 7 is a transverse cross-sectional view of the insulated catheter of FIG. 6 along line 7-7 in FIG. 6.

The catheter can include an insulative annular space 68. FIG. 6 illustrates a longitudinal cross section of a distal portion of insulated catheter 60. FIG. 7 illustrates a transverse cross section of catheter 60 along line 7-7 in FIG. 6. Catheter 60 includes an outer cylindrical wall 62 and an inner cylindrical wall 64, which inner wall 64 defines a lumen 66 for providing cooled infusate. The insulative construction described may, for example, extend for an entire length or for only a portion of catheter 60. The annular space 68 can taper to distal section 70 at a distal end of catheter 60. Annular space 68 can be filled with a biologically safe insulator, including a fluid or gas, such as helium, carbon dioxide, xenon, etc., or other known insulation material such as silica gel, or other materials such as those described in U.S. Pat. Nos. 2,967,152, 3,007,596, and 3,009,600, each of which is expressly incorporated herein in its entirety by reference thereto. The insulation used should not restrict, or should have only minimal impact upon, the flexibility of catheter 60. The annular space 68 can be inflatable and in fluid communication through an inflation lumen with an inflator. In which case, the catheter 60 is inserted into the patient in a low profile state with the annular space 68 deflated so as to facilitate insertion and, once positioned, inflated to provide insulation when cooled infusate is passed through the catheter 60. Upon removal of the device from the patient, the annular space 68 may be evacuated so as to minimize the profile of the catheter 60.

As indicated above, information from at least one of sensors 10a, 10b, 10c, 10d is transmitted to controller 22, which may in turn send signals to pumps 24, 24a, and/or 24b, to adjust flow of infusate, and to cooler 30 and/or heater 31, to adjust a temperature of the infusate, according to a control scheme. As part of such a control scheme, controller 22 may also employ a feedback loop so as to iteratively calculate at a predetermined rate the admixture hematocrit, e.g., the hematocrit of the infusate and blood mixture downstream of the exit region 40, and compare it to a predetermined minimum hematocrit, required to provide sufficient oxygen delivery to the patient. The controller 22 instructs the pump 24 to decrease at least one of an infusion rate and volume of the infusate delivered to the patient and/or instructs the cooler 30 or heater 31 to increase the temperature of the infusate until the admixture hematocrit rises above a predetermined minimum, e.g., 25.

The patient's baseline whole body hematocrit may be measured before the procedure and input by the clinician into the controller 22. During the procedure the whole body hematocrit will change due to the infusion of infusate. Estimates of the patient's whole body hematocrit during the procedure may be determined by serial whole body measurements or calculated by the controller 22, for example, using the following equation:

$$\Delta_{HCT} = \frac{p V_{RBC} \Delta V_{IV}}{V_{IVO}(V_{IVO} + p \Delta V_{IV})}$$

where $V_{RBC}$ is the total blood cell volume, $V_{IVO}$ is the initial total intravascular volume (including $V_{RBC}$), $\Delta V_{IV}$ is the volume of added infusate, and p is the fraction of extracellular water that is intravascular. An initial whole body hematocrit of 0.42 and an initial $V_{IVO}=5.0$ L may be assumed (implying $V_{RBC}=2.1$ L).

In an exemplary embodiment of the present invention, the hematocrit in the blood and infusate mixture, i.e., in the admixture hematocrit (amHct), is calculated by controller 22 using data or measurements from sensors, for example, any of sensors 10a, 10b, 10c, 10d, and using the equation amHct=Hct (1−dF), where dF=IR/(IR+X) and, e.g., when there is no reflux, $X=IR(T_1-T_2)/(T_4-T_1)$. It should be appreciated that the foregoing equations are merely exemplary. Hct represents the whole body hematocrit level of the patient's blood, and dF represents the dilution factor, i.e., the percentage of infusate in the mixture of blood and infusate (when $T_3=T_4$ and reflux is excluded). IR is the infusion rate at which the infusate pump is pumping and X is the free flow contribution, i.e., the flow rate of free or native blood going into the mixture of blood and infusate.

The controller 22 may be configured to account for Hct dilution by taking into account the volume of infusate added to the patient's blood and the volume of the infusion fluid output by the patient, e.g., through urination. The controller 22 may update the whole body hematocrit level of the patient's blood initially input by the clinician into the controller 22 at the beginning of the cooling procedure to reflect dilution according to a computerized function.

The function basically monitors the input or amount of fluid that is added to the patient, i.e., the volume of infused fluid, and monitors the output, i.e., urine output. The input may be automatically calculated and input by the controller 22 by measuring the amount of fluid added, which could be calculated through a number of methods including, but not limited to, subtracting the amount of fluid remaining in the infusate reservoir 30 from the volume of fluid in the reservoir 30 at the beginning of the procedure. The output can be automatically calculated and input or manually input. One method of calculating the change of Hct due to the infusion volume is described in M. A. Neimark, A. A. Konstas, A. F. Laine, J. Pile-Spellman, "Integration of jugular venous return and circle of Willis in a theoretical human model of selective brain cooling," J. Appl. Physiol., 103: 1848-1856, 2007 (first published Aug. 30, 2007), equation 6 on page 4, which references A. A. Konstas, M. A. Neimark, A. F. Laine, J. Pile-Spellman, "A theoretical model of selective cooling using intracarotid cold saline infusion in the human brain," J. Appl. Physiol., 102: 1329-1340, 2007 (first published Dec. 14, 2006), equation 6 page 3, both of which articles are incorporated herein in their entireties by reference thereto.

Alternatively, a calculation to calculate the whole body Hct dilution factor can be performed by assuming that the vast majority of the retained fluid (input−output) will remain intravascular since the intracellular component is small. For example, if we assume that the whole body blood volume is 5 L, the whole body Hct dilution factor (Z) will equal [(input−output)+5 L]/5 L. Whole body Hct/Z will equal adjusted whole body Hct. The calculation of the adjHct will be an iterative process and be continuously updated.

Figure 11:
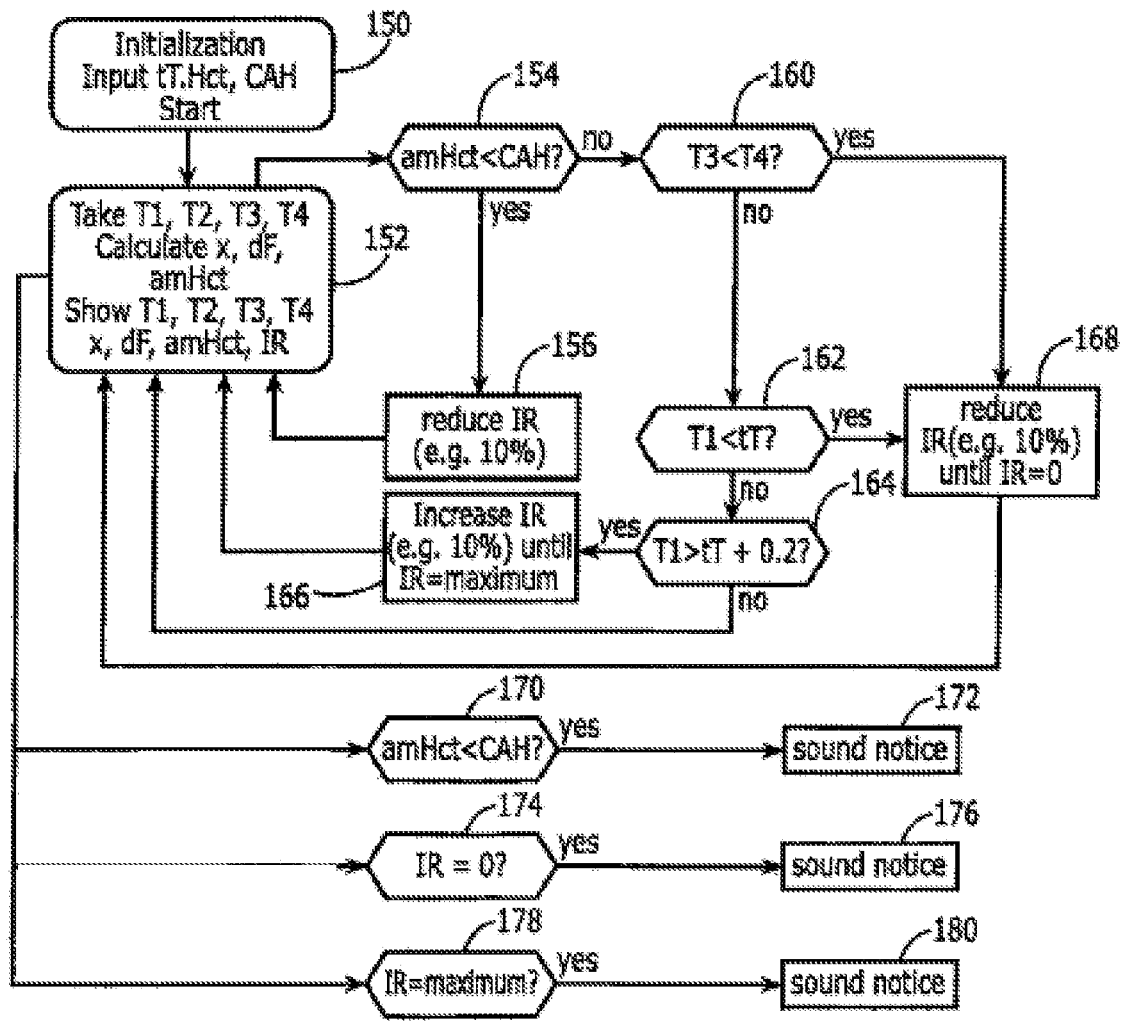
FIG. 11 illustrates an exemplary method for the controller system according to the present invention.

Controller 22 may employ the algorithm laid out in the flow chart of FIG. 11. It should be appreciated that alternative algorithms may be employed, provided that the boundary conditions are met. As used in the chart, $T_1$ represents the most distal sensor, i.e., the temperature of a blood and infusate mixture and $T_2$ represents the infusate temperature as it exits the catheter. Further, $T_3$ is the temperature measured at a "reflux" sensor, for example, about 0.2 to 5 cm proximal to the infusate exit region 40, and $T_4$ represents the core temperature measured by the most proximal sensor, or otherwise calculated or determined. This last sensor is placed along the catheter at a position that would accurately measure the core temperature without interference from the reflux or the infusate. This sensor does not have to be embedded in the catheter. This temperature information may be manually programmed from data obtained by other temperature measurement of the patient. Another variable includes tT, which is the clinical target temperature that is desired to achieve in the target organ or tissue, e.g., selected by the clinician/operator to be programmed into the controller 22.

As indicated above, $T_3$ is the temperature measured at a reflux sensor, e.g., about 0.2 to 5 cm proximal to the infusate exit region 40. It should be appreciated that a location about 0.2 cm proximal to the infusate exit region would be used for organs where there is forward flow of blood during systole and diastole, at all times, whereas a location about 5 cm proximal to the infusate exit region would be used for organs with forward flow only during systole, e.g., the leg. Furthermore, the size of the catheter is also a factor in determining whether the location is closer to 0.2 cm proximal to the infusate exit region or closer to 5 cm proximal to the infusate exit region. In this regard, it should be appreciated that the larger the catheter is in relation to the vessel, the greater the possibility and/or extent of reflux.

In the flow chart of FIG. 11, as reflected in 150, a target temperature (tT) and preset CAH, i.e., a clinically acceptable minimum Hct delivered, for example, to the organ being treated, are chosen by the operator and input into the controller 22. The base whole body hematocrit level (Hat) of the patient's blood, e.g., as determined by analysis of a patient's blood specimen, is determined and also input into the controller 22. In 152, temperature information $T_1$, $T_2$, $T_3$, and $T_4$ are input and the free flow contribution X, dilution factor dF, and the admixture hematocrit level amHct are calculated by controller 22. The $T_1$, $T_2$, $T_3$, and $T_4$ temperatures, the calculated values X, dF, and amHct, as well as the infusion rate IR can be displayed on a control panel for the controller 22, as described below.

In 154, a comparison of the calculated value amHct with a CAH value, i.e., a clinically determined minimum Hct based on routine clinical determination, such as 25, is performed. If amHct is less than the CAH value, a signal goes to 156, which causes the controller 22 to reduce the infusion rate of the infusion pump 24 by a preset amount, such as 10%. For purposes of this chart, reference to pump 24 applies equally to pumps 24a and 24b. If amHct is equal to or greater than the CAH value, the $T_3$ value is compared in 160 with $T_4$. If $T_3$ is not less than $T_4$, i.e., if there is no reflux or a substantial absence of reflux, then $T_1$ is compared in 162 with tT. If $T_1$ is not less than tT, i.e., the mixture of blood and infusate has not reached the target temperature, then $T_1$ is compared in 164 with tT plus a value such as 0.2°. A determination that $T_1$ is not greater than tT plus 0.2° cycles back to 152. However, if it is determined that $T_1$ is greater than tT plus 0.2°, in 166, the rate of the infusion pump 24 is increased by an amount such as 10% until a predetermined maximum infusion pump rate is reached.

When $T_4$ is determined in 160 to be greater than $T_3$, i.e., reflux is detected, or when tT is determined in 162 to be greater than $T_1$, i.e., the target temperature of the blood and infusate mixture has been reached, the rate of the infusion pump IR is reduced by a set percentage or amount, such as 10%, according to the step 168, until IR approaches and/or attains a value of 0. Alternatively, given that the temperature of the blood and infusate mixture may initially be lower than the organ being treated, the controller 22 may wait a predetermined period of time after $T_1$ has reached or dropped below tT before reducing the infusion pump rate.

The infusate may also be delivered at a very high rate with the amHct at the CAH so as to achieve reflux in a short period of time and to cool the organ being treated, e.g., the brain, as much as possible. In this scenario, the temperature of the admixture can drop below the target temperature and the nvFR will slow quickly.

The controller 22 may be programmed to sound alarms or otherwise give feedback or notice upon certain events or occurrences, such as changes in or reaching a minima or maxima for, for example, core temperature, total fluid administration, fluid rate, or admixture hematocrit level. As indicated in 170 and 172, an alarm may sound if amHct is less than CAH. As indicated in 174 and 176, an alarm may sound if the infusion pump 24 stops. Further, as indicated in 178 and 180, an alarm may sound if the rate of the infusion pump 24 reaches a preset maximum value.

Controller 22 may also rely on the reflux of the blood and infusate admixture to calculate the native vessel flow rate (nvFR), dilution factor (dF), and admixture Hct. A control algorithm to this effect can be employed with a device with multiple sensors or with a single sensor, e.g., sensor 10c (FIG. 1). Controller 22 is programmed to ramp up the flow of infusate until reflux is detected, for example, using sensor 10c, and then decrease the flow of infusate to its normal infusion rate. At an infusion rate at or greater than the nvFR reflux occurs. The controller 22 may then set the native vessel flow rate (nvFR) equal to the infusion rate when reflux just occurs.

For example, assuming an infusion rate of 5.0 cc in the blood vessel, a base line infusion rate of 0.5 cc may be "ramped up" by, e.g., 0.5 cc every half second for a total of ten times, until there is reflux. At this point in time T3 would be lower than T4 and it would be known that the infusion rate in the vessel is greater than 4.5 cc but less than 5.5 cc.

Additional iterations could be performed by controller 22 to narrow in on the infusion rate over a smaller and smaller range if desired, repeating the above process with smaller infusion doses. The above process can be reduced to the following general equation:

Flow in the vessel=(Infusate initial rate)+((Infusate Rate Increase)/Interval)*(Number of Interval), where the Number of Intervals is equal to the number of intervals where T3<T4, i.e., when there is reflux of cold infusate.

As can be seen in the equations above, the above determination as to admixture temperature is made without the use of a sensor downstream of the infusate exit region or area 40, e.g., sensor 10a (FIG. 1). This is useful because while sensor 10a provides a temperature reading of the blood and infusate admixture, which may be relied upon as an approximation of the temperature of the organ being cooled, the temperatures of the admixture and organ being cooled do not always coincide especially towards the beginning of cooling. The elimination of the downstream sensor also reduces the overall cost of the device.

The ramping up of the infusate flow until reflux occurs so as to calculate nvFR can also be utilized by the controller 22 to accurately determine when the organ being cooled, e.g., the brain, has reached its target temperature, at which point the controller 22 reduces or stops infusion. The ramping up of the infusate infusion rate and calculation of nvFR may be conducted multiple times, e.g., so as to provide a real-time rapid calculation of nvFR, while the controller 22 monitors the value of the nvFR. Upon detecting a predetermined level of plateauing of the nvFR, i.e., a slope of nvFR over time equal to zero or within a predetermined range above or below zero, which indicates that the organ being cooled has reached its target temperature, the controller 22 may maintain, reduce or stop infusion.

The above determination of target temperature relies on the fact that a plateau in the value of nvFR indicates that the organ being cooled has reached its target temperature. The blood flow of an organ is related to metabolic rate, which in turn is related to temperature. Using the brain as an example, while infusing a constant flow of cold infusate into the internal carotid artery, the temperature of the brain begins to decrease, which in turn decreases the metabolic rate, which in turn decreases the nvFR. As the temperature of the brain approaches the temperature of the cold blood and infusate admixture, it will begin to reach an equilibrium, and thus, the rate of decrease in the temperature of the brain will slow. The temperature of the brain and the admixture will eventually reach an equilibrium and be very similar because the internal carotid artery is an end organ vessel to the brain. At this equilibrium, the temperature of the brain will plateau or may actually begin to increase due to the hemodilution effect of the infusion causing the metabolic needs to increase. Because the temperature of the brain has reached a plateau, the metabolic rate and nvFR will also have reached a plateau. As described above, the controller 22 monitors the value of nvFR, e.g., to detect this plateau, and maintains, reduces, or stops infusion upon such detection.

As further indicated above, the controller 22 may also be adapted to change the volume or flow rate of the infusate or the infusate temperature depending on the nvFR. For example, the controller may be programmed to increase the infusate flow rate or decrease its temperature if the nvFR is not changing fast enough, i.e., the rate of change nvFR is below a predetermined minimum.

Figure 12:
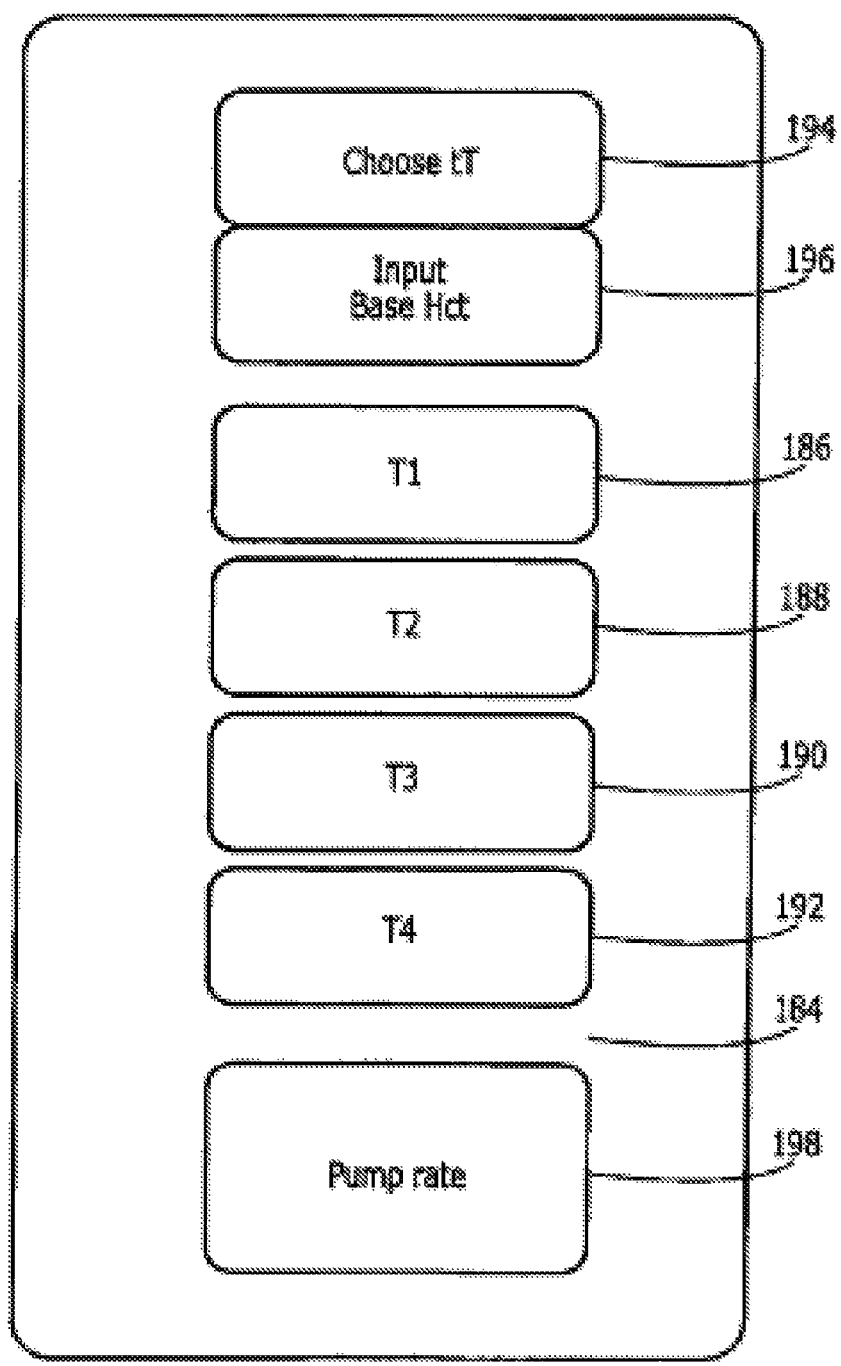
FIG. 12 is a schematic representation of an exemplary embodiment of the control panel according to the present invention.

FIG. 12 is a schematic representation of a control/display panel 184 for the controller 22, e.g., having a touch sensitive screen. The rate of the infusion pump 24 may be shown and controlled at 198. The measured, calculated, or assumed values for $T_1$ to $T_4$ may be displayed at 186, 188, 190, and 192. The value for tT may be selected and displayed at 194, and the Hct value may be input and shown at 196. The nvFR may also be shown on the panel 184.

Exemplary items that can be input in the controller 22 at the beginning of the procedure and may or may not be adjusted during the procedure may include (these may have automatic presets already there but may be adjusted):
target temperature of T1;
whole body Hct;
minimum acceptable whole body Hct;
clinical minimum acceptable Admixture Hct;
temperature desired in reservoirs, e.g., pertaining to single cold reservoir system and hot and cold reservoirs in a two reservoir system;
maximum pressure of infusion;
minimum core body temperature;
maximum volume of fluid to be given;
T3 at which Alarm will trigger;
urine output (most likely inputted at a regular interval by an operator or may be automatic);

Exemplary items to be displayed continuously or triggered (push as button to display) may include:
T1 admixture temperature (likely continuous);
T2 infusion temperature at infusion outflow (likely continuous but could be triggered);
T4 core body temperature (could be continuous or triggered); admixture Hct (likely continuous);
nvFR and graph of nvFR v. time (likely continuous);
T3 temperature upstream of infusion outflow port (continuously displayed, or more preferably, alarmed based or triggered);
volume administered (likely triggered);
temperature of reservoirs (likely triggered); and
whole body adjusted Hct (likely triggered).

Exemplary alarms may include:
reflux (minimum allowed T3 reached);
minimum core body temperature reached;
minimum acceptable Admixture Hct reached;
maximum pressure of infusion reached;
nvFR plateau reached; and
maximum fluid administered.

For illustrative purposes, in no way intended to be limiting, if the target temperature (tT) is set to 33° C. or 306K and the clinically acceptable HCT (CAH) for the blood and infusate mixture to set to 25, the baseline whole body hematocrit (hct) is set to 45, and the infusion rate (IR) of the infusate, which can be a normal saline solution, is set to 30 mL/min at 0° C. or 273K, the sensors 10a, 10b, 10c, 10d may, for example, measure (or controller 22 may calculate) a $T_1$ temperature of 308K, a $T_2$ temperature of 282K, a $T_3$ temperature of 310K, and a $T_4$ temperature of 310K. The controller 22 then calculates the free flow contribution as $$X=IR*(T_1-T_2)/(T_4-T_1)=0.5 \text{ mL/sec } (308K-282K)/(310K-308K),$$

which yields a free flow contribution of 4 mL/sec. The controller 22 also calculates the dilution factor, $$dF=IR/(IR+X)=0.5 \text{ mL/sec}/(0.5 \text{ mL}+4 \text{ mL/sec}),$$

which yields a dilution factor of 0.11. The controller 22 also calculates the hematocrit of the blood and infusate mixture, $$amHct=\text{Base hct}*(1-dF)=45*(1-0.11),$$

which yields a hematocrit of 40.05. Since the amHct is not less than CAH, $T_3$ is not less than $T_4$ (no reflux detected), $T_1$ is not less than the target temperature yet, and $T_1$ is not greater than the target temperature plus 0.2, the current infusion rate may be maintained by the controller 22. Next, $T_1$ to $T_4$ are once again evaluated or measured and the free flow contribution, dilution factor, and admixture hematocrit is recalculated. The process may then repeat consistent with that illustrated in FIG. 11. Alternatively, the infusion rate may be maintained by the controller 22 for a predetermined period of time and the infusion rate may be reduced once the period expires irrespective of whether the conditions above regarding amHct, $T_1$, and $T_4$ are met.

The cooling catheters described and illustrated herein can be used in brain cooling, where cooled infusate is provided to a patient's brain. However, the catheters may have broader use in cooling other organs, tissue, or limbs, or even in the delivery of substances such as pharmaceuticals or other agents to desired sites within a patient's body. The insertion devices and methods described herein may also be used in systems completely independent of the human body and may be used to influence or control any system parameter or a parameter of any flowing material in any type of system.

The infusate delivered by the catheter can be saline solution, such as a commercially available saline solution including about 9% sodium chloride USP, available from, for example, Baxter Healthcare Corporation in Deerfield, Ill. The saline solution can include antioxidants or other vascular agents such as nitric oxide, lidocaine, nitroglycerine, insulin, adenosine, ATP, heat shock proteins, beta blockers, modifiers of calcium channel, modifiers of potassium channel, or other enzymes or metabolism modifiers, etc., or any type of cardiovascular agent or preservation solution, e.g., Washington solution. Modifiers of inflammatory response, modifiers of transmembrane transport, modifiers of lactic acid concentration, or other substances, etc. may also be included. The saline solution can also include delta opiod peptides (e.g., D-Ala2-Leu5-enkephalin DADLE) or other hibernation induction trigger agents, etc. The infusate can be blood, a blood substitute, or a mixture of both.

When the infusate is blood, blood may optionally be removed from the patient for cooling and then returned to the patient, which may be done at a single site to minimize trauma to the patient. In a catheter set, an outer catheter extends only partially into a patient's artery, blood is removed proximally through an annular space between the outer catheter and a distally-extending inner catheter, and cooled blood is returned through the inner catheter.

Brain cooling can be administered in conjunction with a thrombolytic agent such as TPA, heparin, streptokinase, etc. The thrombolytic agent can be administered, e.g., according to conventional protocols prior to, during, and/or subsequent to the brain cooling. Similarly, in the event that surgical or endovascular intervention is indicated in a stroke victim, brain cooling can be administered in conjunction with such a procedure.

To effect vascular brain cooling, standard procedures may be followed. For example, first, a guide catheter is established and then the distal tip of a brain cooling catheter is advanced through the femoral artery, through the aorta, e.g., into the internal, or common, carotid artery. Cooled infusate is perfused through one or more lumens in the brain cooling catheter to the internal carotid artery.

Similar introduction techniques may be used to access other targeted organs or tissue. Cooled blood may be provided to one or more coronary arteries. Hypothermia is believed to be extremely protective of cardiac tissue during ischemia and subsequent reperfusion. A catheter, such as a catheter illustrated in FIG. 8, can be advanced through the aorta and then into the left or right coronary artery. The distal tip of the catheter may then be positioned in the left or right coronary artery at a point proximal to the occlusion or stenosis. A clinician can determine the conditions of treatment in terms of tissue target amHCT, blood flow, and duration, which can be similar to those for brain cooling or supplying cardiac protection during subsequent reperfusion. Infusion can be used as an adjuvant or as definite therapy during angioplasty, thrombolysis, or chemoembolization or delivery of cardio protective agents.

Conventional devices for cooling blood or infusate, for example, during cardiac procedures, can be used to cool infusate to be infused. The device may be compatible with the temperature ranges hereof and may be capable of being controlled by controller 22. An example of such available equipment is the SARNS TCM water bath available from the SARNS Corp. of Ann Arbor, Mich. Such a water bath is used with a cardiopulmonary bypass machine such as the BP40, available from Biomedicus, Minneapolis, Minn. For details regarding brain cooling procedures see, for example, A. E. Schwartz et al., "Isolated Cerebral Hypothermia by Single Carotid Artery perfusion of Extracorporeally Cooled Blood in Baboons," Neurosurgery, Vol. 39, No. 3, September 1996, pp. 577-582, and A. E. Schwartz et al., "Selective Cerebral Hypothermia by Means of Transfemoral Internal Carotid Artery Catheterization," Radiology, Vol. 201, No. 2, November 1996, pp. 571-572, each of which is expressly incorporated herein in its entirety by reference thereto.

Figure 8:
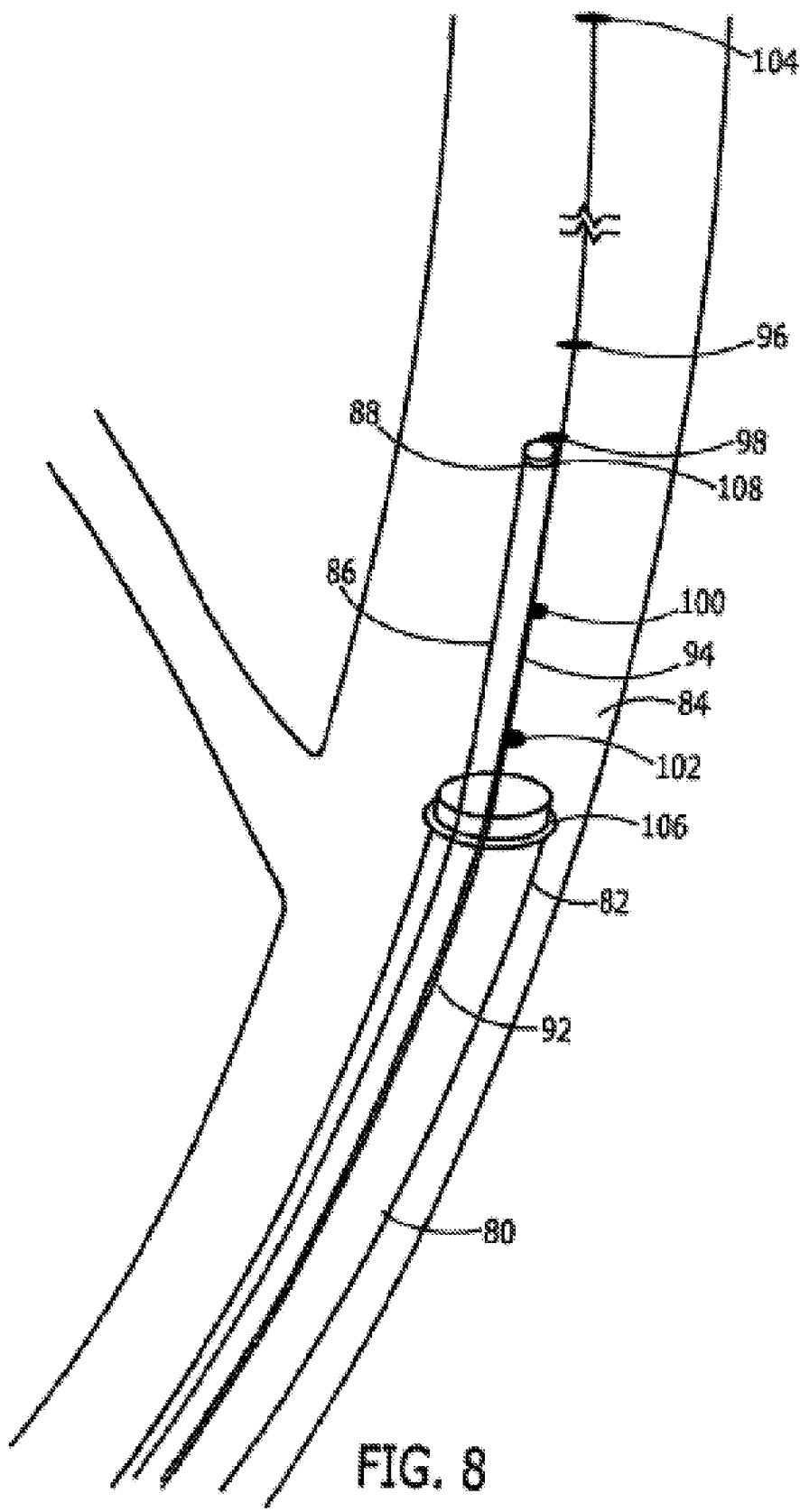
FIG. 8 is a schematic representation of a catheter according town exemplary embodiment of the present invention inserted into a blood vessel of a patient.

As illustrated in FIG. 8, a guide catheter 80 is advanced so that a distal end 82 of catheter 80 is positioned in a patient's carotid artery 84. Extending from distal end 82 is a microcatheter 86 for delivery of infusate. Longitudinally adjacent to microcatheter 86 is a wire 92 having one or more sensors 96, 98, 100, and 102, such as temperature sensors, on its distal section 94. Wire 92 has sensor 96 to measure a parameter of the infusate and blood mixture, sensor 98 to measure a parameter, e.g., the temperature, of the infusate, at a distal end 88 of microcatheter 86, sensor 100 for measuring reflux, and sensor 102 positioned to measure a parameter of the patients blood, for example, the patient's core body temperature. It should be appreciated that a tracer may be measurable and stable, may be picked up by sensors and may have 1st-pass viability (e.g., absorbed completely, excreted completely). The arrangement illustrated in FIG. 8 also includes an optional distal sensor 104 positioned, for example, about 10 to about 25 cm distal to sensor 96, which sensor 104 provides additional distal information.

Catheter distal end 82 and microcatheter distal end 88 can have radiopaque markers 106 and 108, respectively, such as rings or annular bands including tantalum, platinum, gold, etc. Sensors 96, 98, 100, 102, and/or 104 can also include radiopaque material. The radiopaque material facilitates visualization and positioning of the catheter ends 82 and 88 and sensors 96, 98, 100, and 102. For example, marker 108 is just proximal to sensor 98 and marker 106 is well proximal to sensor 102. Other locations of markers and/or sensors are possible. The catheters or microcatheters may optionally have anti-thrombotic and/or lubricious coatings.

The spacing of the sensors may vary. The spacing between sensors 96 and 98 in FIG. 8 may be far enough for sensor 98 to representatively measure the temperature of the infusate and blood mixture, e.g., from about 1 cm to about 10 cm. However, any spacing between sensors 96 and 98 may be provided. Sensor 100 will typically measure the temperature of blood flowing past it. However, the spacing between sensors 98 and 100 may be such that, when blood flow decreases, sensor 100 will pick up the temperature of the reflux. This spacing may be, e.g., from about 0.2 cm to about 5 cm. Sensor 102 may be positioned almost any distance proximal to sensor 100 so long as it measures the temperature of free blood flow. These distances are merely illustrative, and it should be appreciated that the distances may vary dependent upon factors such as the size of the vessel or organ, and/or the application, and/or the materials used, etc.

Wire 92 can include a conventional guidewire construction that is modified to provide a structure for the sensors. Wire 92 may, for example, be about 125 cm to about 175 cm in length and have an outer diameter from about 0.08" to about 0.38". The sensors may be glued, welded, or otherwise firmly affixed to wire 92. Wire 92 may be advanced through a catheter or sheath or independently into the blood vessel.

Figure 9:
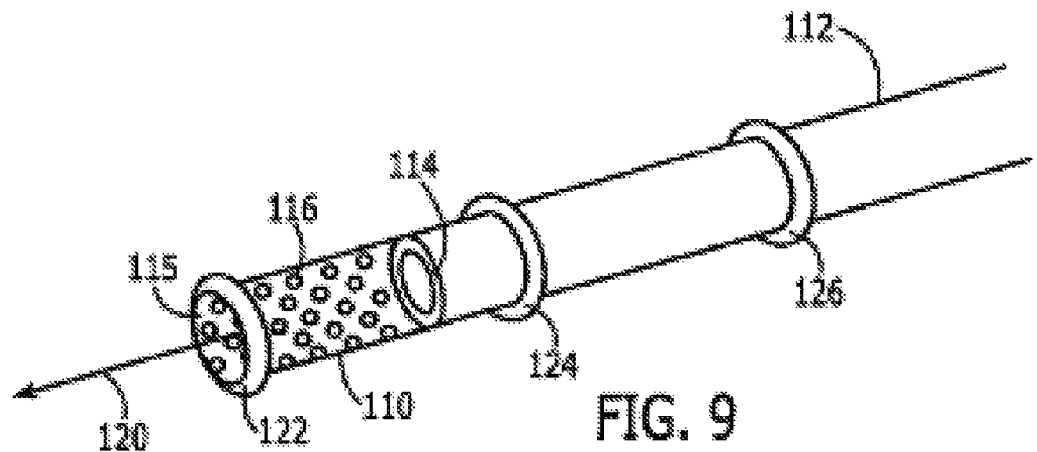
FIG. 9 is a schematic representation of a catheter according to an exemplary embodiment of the present invention.

As illustrated in FIG. 9, a distal portion 110 of a catheter 112 has a single lumen 115 including an inner annular sensor 114 used to measure a parameter of the infusate, for example, the temperature of the infusate. Distal portion 110 has perforations 116 so that blood flowing exterior to catheter 112 mixes with cooled infusate and flow together as an infusate and blood mixture in the direction of arrow 120. Distal annular sensor 122 is positioned to sense, for example, the temperature of the infusate and blood mixture, annular sensor 124 is positioned to detect reflux, and proximal annular sensor 126 is positioned to measure, for example, the body core temperature of the patient.

Sensors 114, 122, 124, and 126 may be spaced relative to each other as described above in connection with FIG. 8. The annular construction of the sensors may be facilitated by use of conductive material such as gold that encircles the catheter surface, to which the sensors may be attached. The sensors may be fixed in place, for example, with a film or other arrangement, to minimize any adverse effects of fluid flowing past.

Figure 10:
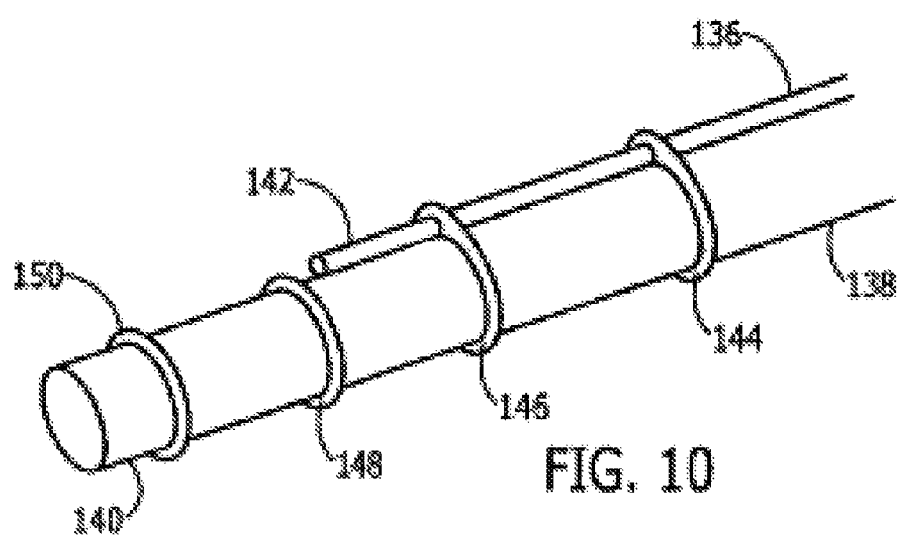
FIG. 10 is a schematic representation of a catheter according to an exemplary embodiment of the present invention.

FIG. 10 illustrates a device that includes a microcatheter 136 connected to and coextensive with catheter 138 along a portion of catheter 138. The distal end 140 of catheter 138 extends pasta distal end 142 of microcatheter 136, for example, for about 1 to about 20 cm. Annular sensor 144 measures, for example, the patient's core temperature and sensor 146 measures, for example, the reflux temperature. Sensor 148 is positioned at or slightly distal to the distal end 142 of microcatheter 136 to measure, for example, the temperature of the infusate. Sensor 148 need not be annular, in which case, it may be positioned circumferentially directly in front of the microcatheter 136. Most distal annular sensor 150 is positioned to measure, for example, the temperature of the mixture of infusate and blood. Microcatheter 136 can be a separate catheter bound to catheter 138 and/or laterally embedded in catheter 138. Microcatheter 136 can also be integrally formed with catheter 138.

The catheters described above can include conventional bio-compatible materials used in the catheter field. For example, the catheters are formed of suitable low-friction bio-compatible polymers such as, for example, extruded polyethylene, polyvinyl chloride, polystyrene, or polypropylene or copolymers thereof, etc. The inner elongated tubular members may have, for example, an outer diameter from about 3 Fr to about 9 Fr and an inner diameter from about 0.038" to about 0.105". The catheter may include a supportive backing, e.g., made from stainless steel or ceramic or fiberglass weave. The ceramic backing has the added benefit of decreasing the heat loss of the cooled infusate as it flows through the insertion device into the patient.

What is claimed is:

1. A method comprising:
   communicating with a source of an infusate;
   controlling at least one of (a) a temperature of the infusate, (b) an infusion rate of the infusate through an insertion device, and (c) a volume of the infusate passing through the insertion device in a downstream direction, in accordance with a temperature of a blood and infusate mixture downstream relative to an infusate exit location of the insertion device while the insertion device is placed in a blood vessel of a patient with a downstream flow of blood for infusion of the infusate, and in accordance with at least one of (a) a temperature of the infusate at least one of at and adjacent the exit location, (b) a temperature upstream and adjacent the exit location, and (c) a core body temperature of the patient;
   receiving signals from a plurality of temperature sensors, at least one of the temperature sensors is positioned downstream relative to the infusate exit location;
   measuring a temperature of the infusate and blood mixture by at least one of the temperature sensors; and
   measuring at least one of (a) the temperature of the infusate adjacent the exit location, (b) the temperature upstream and adjacent the exit location, and (c) the core body temperature of the patient by at least another one of the temperature sensors;
   wherein the temperature sensors include a first temperature sensor positioned downstream relative to an infusate exit location of a catheter and adapted to measure the temperature of the infusate and blood mixture when the catheter is placed in the blood vessel of the patient for infusion of the infusate, a second temperature sensor adapted to measure the temperature of the infusate at least one of at and adjacent the exit location, a third temperature sensor adapted to measure a temperature outside the catheter upstream and adjacent the exit location, and a fourth temperature sensor adapted to measure the core body temperature of the patient.

2. The method according to claim 1, further comprising:
   receiving signals from the temperature sensors; and
   controlling at least one of a heat exchanger and an infusate pump in accordance with the signals from the plurality of temperature sensors.

3. The method according to claim 1, further comprising calculating at least one of (a) a dilution of the blood and (b) a hematocrit downstream the exit location using the equation (Hct)*(1−dF), wherein Hct is a base whole body hematocrit of the patient, dF is the dilution of the blood and is represent by the following equation dF=(infusion rate)/(infusion rate+X), X is an amount of blood per unit time at the core body temperature in the blood and infusate mixture and is represented by the equation X=(infusion rate*(T1−T2)/(T4−T1)), T1 is a temperature as measured by the first temperature sensor, T2 is a temperature as measured by the second temperature sensor, T3 is a temperature as measured by the third temperature sensor, and T4 is a temperature as measured by the fourth temperature sensor.

4. The method according to claim 1, further comprising controlling at least one of (a) the infusion rate of the infusate through the insertion device and (b) a volume of infusate passing through the insertion device in accordance with a hematocrit downstream of the exit location.

5. The method according to claim 1, further comprising calculating at least one parameter of the infusate at least one of at and adjacent the exit location.

6. The method according to claim 5, further comprising calculating the temperature of the infusate at least one of at and adjacent the exit location using at least one of (a) the temperature of the infusate outside the patient, (b) the infusion rate of the infusate through the insertion device, and (c) at least one of a surface area and thermal conductivity of the insertion device.

7. The method according to claim 1, further comprising accepting as input a base whole body hematocrit of the patient (Hct) and to update the Hct based on the volume of infusion fluid passing through the insertion device into the patient and a volume of fluid output by the patient.

8. The method according to claim 1, further comprising controlling the at least one of (a) the temperature of the infusate, (b) the infusion rate of the infusate through the insertion device, and (c) the volume of the infusate passing through the insertion device in accordance with a native vessel blood flow rate in the blood vessel.

9. A method comprising:
communicating with a source of an infusate;
controlling at least one of (a) a temperature of the infusate, (b) an infusion rate of the infusate through an insertion device, and (c) a volume of the infusate passing through the insertion device in a downstream direction, in accordance with a temperature of a blood and infusate mixture downstream relative to an infusate exit location of the insertion device while the insertion device is placed in a blood vessel of a patient with a downstream flow of blood for infusion of the infusate, and in accordance with at least one of (a) a temperature of the infusate at least one of at and adjacent the exit location, (b) a temperature upstream and adjacent the exit location, and (c) a core body temperature of the patient; and
calculating at least one of (a) a dilution of the blood and (b) a hematocrit downstream the exit location using a base whole body hematocrit of the patient (Hct) and the dilution of the blood (dF) based on the equation (Hct)*(1−dF), wherein dF=(infusion rate)/(infusion rate+X), wherein X is an amount of blood per unit time at the core body temperature in the blood and infusate mixture and is represented by the equation X=(infusion rate*(T1−T2)/(T4−T1)), T1 is a temperature of the blood and infusate mixture downstream the exit location, T2 is a temperature of the infusate at least one of at and adjacent the exit location, T3 is temperature adjacent to and upstream the exit location, and T4 is the core body temperature of the patient.

10. A method comprising:
communicating with a source of an infusate;
controlling at least one of (a) a temperature of the infusate, (b) an infusion rate of the infusate through an insertion device, and (c) a volume of the infusate passing through the insertion device in a downstream direction, in accordance with a temperature of a blood and infusate mixture downstream relative to an infusate exit location of the insertion device while the insertion device is placed in a blood vessel of a patient with a downstream flow of blood for infusion of the infusate, and in accordance with at least one of (a) a temperature of the infusate at least one of at and adjacent the exit location, (b) a temperature upstream and adjacent the exit location, and (c) a core body temperature of the patient;

controlling flow of infusate from a first pressurized reservoir of infusate at a first temperature through the insertion device;
controlling flow of infusate from a second pressurized reservoir of infusate at a second temperature through the insertion device; and
controlling the temperature of the infusate flowing through the insertion device via coordinated control of both the flow of infusate from the first pressurized reservoir and the flow of infusate from the second pressurized reservoir.

11. A method, comprising:
communicating with a source of an infusate;
receiving signals from a sensor located exterior to an internal lumen of an insertion device positioned in a system filled with at least one of a fluid and gas flowing in a first direction, the signals indicative of at least one parameter of at least one of the fluid and gas to control at least one of (a) at least one parameter of the infusate, (b) an infusion rate of the infusate through the insertion device, and (c) a volume of the infusate passing through the insertion device in accordance with the signals from the sensor, wherein the sensor is located a distance away from an infusate exit location of the insertion device along a second direction opposite the first direction; and
detecting reflux and calculating at least one of (i) a native vessel flow rate in a blood vessel in which the insertion device is inserted, (ii) a dilution factor of the blood in the blood vessel, (iii) a hematocrit of a mixture of the blood and infusate in the blood vessel, and (iv) a temperature of the blood and infusate mixture in the blood vessel in accordance with a determination as to when reflux occurs.

12. The method according to claim 11, further comprising increasing the infusion rate of the infusate until reflux is achieved.

13. The method according to claim 11, further comprising:
calculating a native vessel flow rate in a blood vessel in which the insertion device is inserted; and
controlling at least one of a temperature, the volume, and the flow rate of the infusate into the patient based on the native vessel flow rate.

14. The method according to claim 11, further comprising:
communicating with a source of an infusate;
receiving signals from a sensor located exterior to an internal lumen of an insertion device positioned in a system filled with at least one of a fluid and gas flowing in a first direction, the signals indicative of at least one parameter of at least one of the fluid and gas to control at least one of (a) at least one parameter of the infusate, (b) an infusion rate of the infusate through the insertion device, and (c) a volume of the infusate passing through the insertion device in accordance with the signals from the sensor, wherein the sensor is located a distance away from an infusate exit location of the insertion device along a second direction opposite the first direction;
calculating a native vessel flow rate in a blood vessel in which the insertion device is inserted;
monitoring a plateauing of the native vessel flow rate; and
performing at least one of stop, maintain, and reduce infusion of the infusate into the patient upon detection of the plateauing of the native vessel flow rate.

* * * * *